US012750593B2

(12) United States Patent
He

(10) Patent No.: US 12,750,593 B2
(45) **Date of Patent: *Sep. 29, 2026**

(54) DEPTH-BASED AUTO-EXPOSURE MANAGEMENT

(71) Applicant: Intuitive Surgical Operations, Inc., Sunnyvale, CA (US)

(72) Inventor: Zhen He, Cupertino, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 325 days.

This patent is subject to a terminal disclaimer.

(21) Appl. No.: 18/564,367

(22) PCT Filed: Jun. 14, 2022

(86) PCT No.: PCT/US2022/033477
§ 371 (c)(1),
(2) Date: Nov. 27, 2023

(87) PCT Pub. No.: WO2022/266131
PCT Pub. Date: Dec. 22, 2022

(65) Prior Publication Data

US 2024/0259696 A1 Aug. 1, 2024

Related U.S. Application Data

(60) Provisional application No. 63/210,828, filed on Jun. 15, 2021.

(51) Int. Cl.
*H04N 23/76* (2023.01)
*A61B 1/00* (2006.01)
(Continued)

(52) U.S. Cl.
CPC ....... *H04N 23/76* (2023.01); *A61B 1/000095* (2022.02); *A61B 1/00193* (2013.01);
(Continued)

(58) Field of Classification Search
CPC .... H04N 23/76; H04N 13/204; H04N 13/271; H04N 23/555; H04N 23/611;
(Continued)

(56) References Cited

U.S. PATENT DOCUMENTS

2014/0267626 A1* 9/2014 Lilagan .............. A61B 1/00193 348/46
2019/0099081 A1* 4/2019 Horesh ................ A61B 5/0071

FOREIGN PATENT DOCUMENTS

EP 3469978 A1 4/2019

OTHER PUBLICATIONS

International Preliminary Report on Patentability for Application No. PCT/US2022/033477, mailed Dec. 28, 2023, 10 pages.
(Continued)

*Primary Examiner* — Sinh Tran
*Assistant Examiner* — Angel L Garces-Rivera

(57) ABSTRACT

The present application is a U.S. National Stage Application under 35 U.S.C. § 371 of International Application No. PCT/US2022/033477, filed on Jun. 14, 2022, which claims priority to U.S. Provisional Patent Application No. 63/210, 828, filed Jun. 15, 2021, each of which is hereby incorporated by reference in its entirety.

19 Claims, 13 Drawing Sheets

(51) Int. Cl.

| | |
|---|---|
| ***A61B 1/04*** | (2006.01) |
| ***A61B 1/313*** | (2006.01) |
| ***G06T 7/20*** | (2017.01) |
| ***G06T 7/593*** | (2017.01) |
| ***G06T 7/70*** | (2017.01) |
| ***H04N 13/00*** | (2018.01) |
| ***H04N 13/204*** | (2018.01) |
| ***H04N 13/271*** | (2018.01) |
| ***H04N 23/50*** | (2023.01) |
| ***H04N 23/611*** | (2023.01) |
| ***H04N 23/71*** | (2023.01) |
| ***H04N 23/72*** | (2023.01) |
| ***H04N 23/73*** | (2023.01) |
| ***H04N 23/74*** | (2023.01) |

(52) U.S. Cl.

CPC .................. *A61B 1/04* (2013.01); *G06T 7/20* (2013.01); *G06T 7/593* (2017.01); *G06T 7/70* (2017.01); *H04N 13/204* (2018.05); *H04N 13/271* (2018.05); *H04N 23/555* (2023.01); *H04N 23/611* (2023.01); *H04N 23/71* (2023.01); *H04N 23/72* (2023.01); *H04N 23/74* (2023.01); *A61B 1/3132* (2013.01); *G06T 2207/10068* (2013.01); *G06T 2207/30004* (2013.01); *H04N 2013/0081* (2013.01); *H04N 23/73* (2023.01)

(58) Field of Classification Search

CPC ........ H04N 23/71; H04N 23/72; H04N 23/74; H04N 23/73; H04N 2013/0081; A61B 1/000095; A61B 1/00193; A61B 1/04; A61B 1/3132; G06T 7/20; G06T 7/593; G06T 7/70; G06T 2207/10068; G06T 2207/30004

See application file for complete search history.

(56) References Cited

OTHER PUBLICATIONS

International Search Report and Written Opinion for Application No. PCT/US2022/33477, mailed Sep. 29, 2022, 13 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner 900-1

802

| | | | | | | | | | | | | | | | | | | | | | | | | | |
|---|---|---|---|---|---|---|---|---|---|---|---|---|---|---|---|---|---|---|---|---|---|---|---|---|---|
| 0 | 0 | 0 | 0 | 0 | 0 | 1 | 1 | 2 | 2 | 3 | 3 | 4 | 4 | 3 | 3 | 2 | 2 | 1 | 1 | 0 | 0 | 0 | 0 | 0 | 0 |
| 0 | 0 | 0 | 0 | 0 | 1 | 1 | 2 | 2 | 3 | 3 | 4 | 4 | 4 | 4 | 3 | 3 | 2 | 2 | 1 | 1 | 0 | 0 | 0 | 0 | 0 |
| 0 | 0 | 0 | 0 | 1 | 1 | 2 | 2 | 3 | 3 | 4 | 4 | 5 | 5 | 4 | 4 | 3 | 3 | 2 | 2 | 1 | 1 | 0 | 0 | 0 | 0 |
| 0 | 0 | 0 | 1 | 1 | 2 | 2 | 3 | 3 | 4 | 4 | 5 | 5 | 5 | 5 | 4 | 4 | 3 | 3 | 2 | 2 | 1 | 1 | 0 | 0 | 0 |
| 0 | 0 | 1 | 1 | 2 | 2 | 3 | 3 | 4 | 4 | 5 | 5 | 6 | 6 | 5 | 5 | 4 | 4 | 3 | 3 | 2 | 2 | 1 | 1 | 0 | 0 |
| 0 | 1 | 1 | 2 | 2 | 3 | 3 | 4 | 4 | 5 | 5 | 6 | 6 | 6 | 6 | 5 | 5 | 4 | 4 | 3 | 3 | 2 | 2 | 1 | 1 | 0 |
| 1 | 1 | 2 | 2 | 3 | 3 | 4 | 4 | 5 | 5 | 6 | 6 | 7 | 7 | 6 | 6 | 5 | 5 | 4 | 4 | 3 | 3 | 2 | 2 | 1 | 1 |
| 1 | 2 | 2 | 3 | 3 | 4 | 4 | 5 | 5 | 6 | 6 | 7 | 7 | 7 | 7 | 6 | 6 | 5 | 5 | 4 | 4 | 3 | 3 | 2 | 2 | 1 |
| 2 | 2 | 3 | 3 | 4 | 4 | 5 | 5 | 6 | 6 | [illegible] | 7 | 8 | 8 | 7 | 7 | 6 | 6 | 5 | 5 | 4 | 4 | 3 | 3 | 2 | 2 |
| 2 | 3 | 3 | 4 | 4 | 5 | 5 | 6 | 6 | 7 | [illegible] | [illegible] | 8 | 8 | 8 | 7 | 7 | 6 | 6 | 5 | 5 | 4 | 4 | 3 | 3 | 2 |
| 3 | 3 | 4 | 4 | 5 | 5 | 6 | 6 | 7 | 7 | 8 | 8 | 9 | 9 | 8 | 8 | 7 | 7 | 6 | 6 | 5 | 5 | 4 | 4 | 3 | 3 |
| 3 | 3 | 4 | 4 | 5 | 5 | 6 | 6 | 7 | 7 | 8 | 8 | 9 | 9 | 8 | 8 | 7 | 7 | 6 | 6 | 5 | 5 | 4 | 4 | 3 | 3 |
| 2 | 3 | 3 | 4 | 4 | 5 | 5 | 6 | 6 | 7 | 7 | 8 | 8 | 8 | 8 | 7 | 7 | 6 | 6 | 5 | 5 | 4 | 4 | 3 | 3 | 2 |
| 2 | 2 | 3 | 3 | 4 | 4 | 5 | 5 | 6 | 6 | 7 | 7 | 8 | 8 | 7 | 7 | 6 | 6 | 5 | 5 | 4 | 4 | 3 | 3 | 2 | 2 |
| 1 | 2 | 2 | 3 | 3 | 4 | 4 | 5 | 5 | 6 | 6 | 7 | 7 | 7 | 7 | 6 | 6 | 5 | 5 | 4 | 4 | 3 | 3 | 2 | 2 | 1 |
| 1 | 1 | 2 | 2 | 3 | 3 | 4 | 4 | 5 | 5 | 6 | 6 | 7 | 7 | 6 | 6 | 5 | 5 | 4 | 4 | 3 | 3 | 2 | 2 | 1 | 1 |
| 0 | 1 | 1 | 2 | 2 | 3 | 3 | 4 | 4 | 5 | 5 | 6 | 6 | 6 | 6 | 5 | 5 | 4 | 4 | 3 | 3 | 2 | 2 | 1 | 1 | 0 |
| 0 | 0 | 1 | 1 | 2 | 2 | 3 | 3 | 4 | 4 | 5 | 5 | 6 | 6 | 5 | 5 | 4 | 4 | 3 | 3 | 2 | 2 | 1 | 1 | 0 | 0 |
| 0 | 0 | 0 | 1 | 1 | 2 | 2 | 3 | 3 | 4 | 4 | 5 | 5 | 5 | 5 | 4 | 4 | 3 | 3 | 2 | 2 | 1 | 1 | 0 | 0 | 0 |
| 0 | 0 | 0 | 0 | 1 | 1 | 2 | 2 | 3 | 3 | 4 | 4 | 5 | 5 | 4 | 4 | 3 | 3 | 2 | 2 | 1 | 1 | 0 | 0 | 0 | 0 |
| 0 | 0 | 0 | 0 | 0 | 1 | 1 | 2 | 2 | 3 | 3 | 4 | 4 | 4 | 4 | 3 | 3 | 2 | 2 | 1 | 1 | 0 | 0 | 0 | 0 | 0 |
| 0 | 0 | 0 | 0 | 0 | 0 | 1 | 1 | 2 | 2 | 3 | 3 | 4 | 4 | 3 | 3 | 2 | 2 | 1 | 1 | 0 | 0 | 0 | 0 | 0 | 0 |

900-2

804

| | | | | | | | | | | | | | | | | | | | | | | | | | |
|---|---|---|---|---|---|---|---|---|---|---|---|---|---|---|---|---|---|---|---|---|---|---|---|---|---|
| 2 | 2 | 3 | 3 | 4 | 4 | 5 | 5 | 6 | 6 | 6 | 6 | 5 | 5 | 4 | 4 | 3 | 3 | 2 | 2 | 1 | 1 | 0 | 0 | 0 | 0 |
| 2 | 3 | 3 | 4 | 4 | 5 | 5 | 6 | 6 | 7 | 7 | 6 | 6 | 5 | 5 | 4 | 4 | 3 | 3 | 2 | 2 | 1 | 1 | 0 | 0 | 0 |
| 3 | 3 | 4 | 4 | 5 | 5 | 6 | 6 | 7 | 7 | 7 | 7 | 6 | 6 | 5 | 5 | 4 | 4 | 3 | 3 | 2 | 2 | 1 | 1 | 0 | 0 |
| 3 | 4 | 4 | 5 | 5 | 6 | 6 | [illegible] | 7 | 8 | 8 | 7 | 7 | 6 | 6 | 5 | 5 | 4 | 4 | 3 | 3 | 2 | 2 | 1 | 1 | 0 |
| 4 | 4 | 5 | 5 | 6 | 6 | 7 | [illegible] | [illegible] | 8 | 8 | 8 | 7 | 7 | 6 | 6 | 5 | 5 | 4 | 4 | 3 | 3 | 2 | 2 | 1 | 1 |
| 4 | 5 | 5 | 6 | 6 | 7 | 7 | 8 | 8 | 9 | 9 | 8 | 8 | 7 | 7 | 6 | 6 | 5 | 5 | 4 | 4 | 3 | 3 | 2 | 2 | 1 |
| 4 | 5 | 5 | 6 | 6 | 7 | 7 | 8 | 8 | 9 | 9 | 8 | 8 | 7 | 7 | 6 | 6 | 5 | 5 | 4 | 4 | 3 | 3 | 2 | 2 | 1 |
| 4 | 4 | 5 | 5 | 6 | 6 | 7 | 7 | 8 | 8 | 8 | 8 | 7 | 7 | 6 | 6 | 5 | 5 | 4 | 4 | 3 | 3 | 2 | 2 | 1 | 1 |
| 3 | 4 | 4 | 5 | 5 | 6 | 6 | 7 | 7 | 8 | 8 | 7 | 7 | 6 | 6 | 5 | 5 | 4 | 4 | 3 | 3 | 2 | 2 | 1 | 1 | 0 |
| 3 | 3 | 4 | 4 | 5 | 5 | 6 | 6 | 7 | 7 | 7 | 7 | 6 | 6 | 5 | 5 | 4 | 4 | 3 | 3 | 2 | 2 | 1 | 1 | 0 | 0 |
| 2 | 3 | 3 | 4 | 4 | 5 | 5 | 6 | 6 | 7 | 7 | 6 | 6 | 5 | 5 | 4 | 4 | 3 | 3 | 2 | 2 | 1 | 1 | 0 | 0 | 0 |
| 2 | 2 | 3 | 3 | 4 | 4 | 5 | 5 | 6 | 6 | 6 | 6 | 5 | 5 | 4 | 4 | 3 | 3 | 2 | 2 | 1 | 1 | 0 | 0 | 0 | 0 |
| 1 | 2 | 2 | 3 | 3 | 4 | 4 | 5 | 5 | 6 | 6 | 5 | 5 | 4 | 4 | 3 | 3 | 2 | 2 | 1 | 1 | 0 | 0 | 0 | 0 | 0 |
| 1 | 1 | 2 | 2 | 3 | 3 | 4 | 4 | 5 | 5 | 5 | 5 | 4 | 4 | 3 | 3 | 2 | 2 | 1 | 1 | 0 | 0 | 0 | 0 | 0 | 0 |
| 0 | 1 | 1 | 2 | 2 | 3 | 3 | 4 | 4 | 5 | 5 | 4 | 4 | 3 | 3 | 2 | 2 | 1 | 1 | 0 | 0 | 0 | 0 | 0 | 0 | 0 |
| 0 | 0 | 1 | 1 | 2 | 2 | 3 | 3 | 4 | 4 | 4 | 4 | 3 | 3 | 2 | 2 | 1 | 1 | 0 | 0 | 0 | 0 | 0 | 0 | 0 | 0 |
| 0 | 0 | 0 | 1 | 1 | 2 | 2 | 3 | 3 | 4 | 4 | 3 | 3 | 2 | 2 | 1 | 1 | 0 | 0 | 0 | 0 | 0 | 0 | 0 | 0 | 0 |
| 0 | 0 | 0 | 0 | 1 | 1 | 2 | 2 | 3 | 3 | 3 | 3 | 2 | 2 | 1 | 1 | 0 | 0 | 0 | 0 | 0 | 0 | 0 | 0 | 0 | 0 |
| 0 | 0 | 0 | 0 | 0 | 1 | 1 | 2 | 2 | 3 | 3 | 2 | 2 | 1 | 1 | 0 | 0 | 0 | 0 | 0 | 0 | 0 | 0 | 0 | 0 | 0 |
| 0 | 0 | 0 | 0 | 0 | 0 | 1 | 1 | 2 | 2 | 2 | 2 | 1 | 1 | 0 | 0 | 0 | 0 | 0 | 0 | 0 | 0 | 0 | 0 | 0 | 0 |
| 0 | 0 | 0 | 0 | 0 | 0 | 0 | 1 | 1 | 2 | 2 | 1 | 1 | 0 | 0 | 0 | 0 | 0 | 0 | 0 | 0 | 0 | 0 | 0 | 0 | 0 |
| 0 | 0 | 0 | 0 | 0 | 0 | 0 | 0 | 1 | 1 | 1 | 1 | 0 | 0 | 0 | 0 | 0 | 0 | 0 | 0 | 0 | 0 | 0 | 0 | 0 | 0 |

Fig. 9

DEPTH-BASED AUTO-EXPOSURE MANAGEMENT

RELATED APPLICATIONS

The present application claims priority to U.S. Provisional Patent Application No. 63/210,828, filed Jun. 15, 2021, the contents of which is hereby incorporated by reference in its entirety.

BACKGROUND INFORMATION

Auto-exposure algorithms are used when images are captured and processed to help ensure that content depicted in the images is properly exposed (e.g., neither underexposed so as to look too dark nor overexposed so as to look too bright). While conventional auto-exposure algorithms adequately serve many types of images, these algorithms may be suboptimal or inadequate in various ways when operating on images depicting scenes with certain characteristics. For instance, an image will be considered that depicts a relatively confined space that is illuminated with artificial light from a light source near the device capturing the image. In this scenario, certain foreground content (e.g., content relatively proximate to the light source and image capture device) may be illuminated with significantly more intensity than certain background content, and, as such, may call for a different auto-exposure approach than the background content.

Conventional auto-exposure algorithms typically do not identify proximity differences between foreground and background content, much less account for these differences in a manner that allows auto-exposure algorithms to prioritize the most important content. Consequently, these types of images may be overexposed or underexposed in their entirety, or, in some cases, less important content within the images (e.g., background content) may be properly exposed at the expense of more important content (e.g., foreground content) being overexposed or underexposed. In either case, detail of the image may be lost or obscured.

SUMMARY

The following description presents a simplified summary of one or more aspects of the apparatuses, systems, and methods described herein. This summary is not an extensive overview of all contemplated aspects and is intended to neither identify key or critical elements of all aspects nor delineate the scope of any or all aspects, Its sole purpose is to present one or more aspects of the systems and methods described herein as a prelude to the detailed description that is presented below.

An illustrative apparatus for depth-based auto-exposure management may include one or more processors and memory storing executable instructions that, when executed by the one or more processors, cause the apparatus to perform various operations described herein. For example, the apparatus may obtain a depth map corresponding to an image frame captured by an image capture system in accordance with an auto-exposure parameter set to a first setting. The apparatus may also obtain an object map corresponding to the image frame. The depth map may indicate depth values for pixel units of the image frame, and the object map may indicate which of the pixel units depict an object of a predetermined object type. Based on the depth map and the object map, the apparatus may determine an auto-exposure gain associated with the image frame. Based on the auto-exposure gain, the apparatus may determine a second setting for the auto-exposure parameter. The second setting may be configured to be used by the image capture system to capture a subsequent image frame.

An illustrative method for depth-based auto-exposure management may include various operations described herein, each of which may be performed by a computing device such as an auto-exposure management apparatus described herein. For example, the method may include obtaining a depth map corresponding to an image frame captured by an image capture system in accordance with an auto-exposure parameter set to a first setting. The depth map may indicate depth values for pixel units of the image frame. The method may also include generating, based on the depth map, a specular threshold map corresponding to the image frame. The specular threshold map may indicate specular thresholds for the pixel units. The method may further include determining, based on the specular threshold map, an auto-exposure gain associated with the image frame, as well as determining, based on the auto-exposure gain, a second setting for the auto-exposure parameter. The second setting may be configured to be used by the image capture system to capture a subsequent image frame.

An illustrative non-transitory computer-readable medium may store instructions that, when executed, cause one or more processors of a computing device to perform various operations described herein. For example, the one or more processors may obtain a depth map corresponding to an image frame captured by an image capture system in accordance with an auto-exposure parameter set to a first setting. The one or more processors may also obtain an object map corresponding to the image frame. The depth map may indicate depth values for pixel units of the image frame and the object map may indicate which of the pixel units depict an object of a predetermined object type. Based on the depth map and the object map, the one or more processors may determine an auto-exposure gain associated with the image frame. The one or more processors may also determine a second setting for the auto-exposure parameter based on the auto-exposure gain. The second setting may be configured to be used by the image capture system to capture a subsequent image frame.

An illustrative system for auto-exposure management of multi-component images may include an illumination source configured to illuminate tissue within a body during a performance of a medical procedure, an image capture device configured to capture an image frame in accordance with an auto-exposure parameter set to a first setting, and one or more processors. The image frame may depict an internal view of the body that features the tissue illuminated by the illumination source. The one or more processors may be configured to generate, based on a depth map corresponding to the image frame, a specular threshold map corresponding to the image frame. The depth map may indicate depth values for pixel units of the image frame and the specular threshold map may indicate specular thresholds for the pixel units. Based on the specular threshold map and an object map that indicates which of the pixel units depict an object of a predetermined object type, the one or more processors may determine an auto-exposure gain associated with the image frame. Based on the auto-exposure gain, the one or more processors may determine a second setting for the auto-exposure parameter. The second setting may be configured to be used by the image capture system to capture a subsequent image frame.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 shows two illustrative spatial status maps corresponding to the image frame of FIG. 6 in accordance with principles described herein.

DETAILED DESCRIPTION

Figure 1:
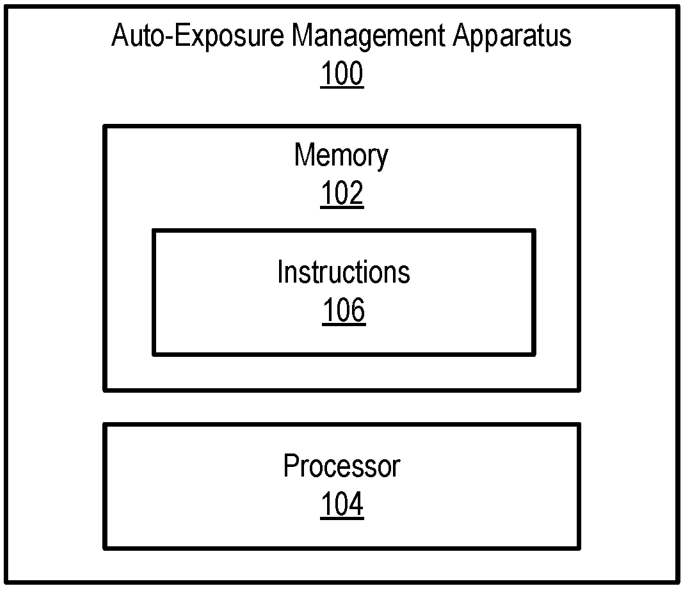
FIG. 1 shows an illustrative auto-exposure management apparatus for depth-based auto-exposure management in accordance with principles described herein.

Apparatuses, methods, and systems for depth-based auto-exposure management are described herein. As will be described in detail, auto-exposure management may be significantly improved over conventional approaches by employing novel techniques that identify and account in various ways for depth (e.g., relative distance from an image capture device) of content at a scene being depicted by a series of image frames.

Auto-exposure management may involve setting various types of auto-exposure parameters associated with an image capture system and/or a component thereof. For instance, auto-exposure parameters may be associated with a camera or other image capture device included in the image capture system, an illumination source operating with the image capture device, an analysis module that processes data captured by the image capture device, communicative components of the system, or the like. A few non-limiting examples of auto-exposure parameters that may be managed by an auto-exposure management system may include exposure time, shutter aperture, illumination intensity, various luminance gains (e.g., an analog gain, a Red-Green-Blue (RGB) gain, a Bayer gain, etc.), and so forth.

Auto-exposure algorithms operate by determining how much light is present in a scene (e.g., based on an analysis of one image of the scene), and attempting to optimize the auto-exposure parameters of an image capture system to cause the image capture system to provide a desired amount of exposure (e.g., for subsequent images that are to be captured by the image capture system). Conventionally, such auto-exposure algorithms have been configured to set auto-exposure parameters exclusively based on scene content characteristics such as luminance and/or chrominance without accounting for depth of content at the scene being depicted. There may be several reasons why depth has generally been ignored for auto-exposure management purposes. As one example, depth information may not be available or easily obtainable in many situations. As another example, different depths of different content depicted in an image frame sequence may not significantly impact the success of auto-exposure management for the image frame sequence under many conditions (e.g., based on various aspects of lighting and/or other scene attributes).

Despite these reasons, however, it may be the case in certain situations that accounting for depth information significantly improves the success of auto-exposure management of image frames being captured. For example, a scene will be considered that is relatively close to the device performing the capture and that is primarily or exclusively illuminated by a light source associated with the image capture device (e.g., a flash; an illumination source in a darkened, enclosed location; etc.) rather than ambient light from other light sources that are farther away from the scene content. In this example, depth differences between foreground and background content at the scene may significantly impact how well illuminated the content appears to be in the captured images. This is because light intensity falls off according to an inverse square law in a manner that causes more dramatic differences in illumination for content close to a light source than content that is farther away or illuminated by multiple ambient light sources. Accordingly, principles described herein are capable of greatly improving auto-exposure management results in these and other situations when depth data is available (or reasonably attainable by available detection methods) and is accounted for in ways described herein.

While implementations described herein may find application with a variety of different types of images captured or generated in various use cases by different types of image processing systems, a particular illustrative use case related to endoscopic medical imaging will be used throughout this description to describe and illustrate principles of depth-based auto-exposure management. Endoscopic medical imaging provides a productive illustration of one type of imaging situation that can be positively impacted by depth-based auto-exposure management described herein for several reasons.

A first reason that endoscopic imaging scenarios provide a productive example is that endoscopic imaging is typically performed internally to a body in enclosed and relatively tight spaces that are dark but for illumination provided by an artificial light source associated with the endoscopic device. Accordingly, the circumstances described above come into play in which illumination intensity differences between objects in close proximity (to one another and to the light source) may be relatively dramatic due to the close proximity and the inverse square law governing how light intensity diminishes with distance from the source (e.g., content twice as far from the light source, which may only be a few centimeters in such a small space, is illuminated with one-fourth the light intensity, etc.). As a result of these circumstances, foreground content (e.g., scene content that is a closer to the image capture device and the corresponding illumination source providing much or all the light for the scene) may tend to be overexposed, particularly if the foreground content takes up a relatively small portion of image frames being captured such that the background content has the larger impact on auto-exposure management. Additionally, this issue may be compounded further for auto-exposure algorithms that detect and deemphasize specular pixels (e.g., pixels that directly reflect light from the light source to form a glare that is so bright as to be unrecoverable or otherwise not worth accounting for in auto-exposure decisions). Specifically, foreground content that is closer to the illumination source may be detected to include many false specular pixels (e.g., pixels that are not actually specular pixels but are just extra bright due to their close proximity to the illumination source). As such, these pixels may be ignored by the auto-exposure algorithm when it would be desirable that they should be accounted for.

Another reason that endoscopic imaging scenarios provide a productive use case scenario for describing principles of depth-based auto-exposure management is that it may be common during a medical procedure being depicted by an endoscopic image capture device for different content to have different depths that impact auto-exposure management significantly. For example, while a surgeon (or other user) is performing a medical procedure inside a body using endoscopic imaging, the surgeon may often wish to examine a particular tissue sample up close and may bring that tissue closer to the endoscopic image capture device to get a better look. If the auto-exposure algorithm prioritizes exposure for the background content over this foreground tissue sample that the user is most interested in (or, worse, treats this tissue sample as being composed of specular pixels that are to be ignored), the situation may be undesirable and frustrating to the user because the content he or she considers most important at the moment is difficult to see in detail (e.g., due to being overexposed) as the algorithm prioritizes the less important background content. Accordingly, depth-based auto-exposure management principles described herein have a potential to significantly improve the user's experience in these common situations when a tissue sample is held close to the camera.

Yet another reason that endoscopic imaging scenarios provide a productive use case scenario for describing principles of depth-based auto-exposure management is that, unlike many imaging scenarios (e.g., single lens point-and-shoot cameras, etc.), endoscopic image capture devices are commonly configured in a manner that makes depth data for the scene available or readily attainable. For example, endoscopic image capture devices may be configured to capture stereoscopic imagery such that slightly different perspectives can be presented to each eye of the user (e.g., the surgeon) to provide a sense of depth to the scene. Because these stereoscopic versions of each image frame may be available from the endoscopic image capture device, a depth map may be generated for each image frame based on differences between corresponding features that are depicted in both versions of the stereoscopic image frame. This depth map may then be used for various aspects of depth-based auto-exposure management described herein.

As will be described in more detail below, depth-based auto-exposure management implementations described herein may employ depth data to improve auto-exposure management outcomes in at least two ways.

First, implementations described herein may differentiate, recognize, and track different types of content in order to prioritize how the different types of content are to be analyzed by auto-exposure algorithms described herein. In particular, it may be desirable to prioritize tissue that a surgeon holds close to the camera for examination while it may not be desirable to give such priority to instrumentation that may incidentally be close to the capture device but is not of particular interest to the surgeon (indeed, it may even be desirable for such content to be deprioritized or deemphasized). Accordingly, along with accounting for depth of different objects, implementations described herein may further account for the object type of foreground objects so as to prioritize objects of interest to the user (e.g., tissue samples) while not giving undue priority to foreground objects not of interest to the user (e.g., instrumentation).

Second, implementations described herein may account for proximity and illumination fall-off principles mentioned above to make specular rejection algorithms more robust and accurate. In particular, specular thresholds (e.g., thresholds that, when satisfied, cause a particular pixel to be designated as a specular pixel that is to be deemphasized or ignored by the auto-exposure algorithm) may be adjusted in accordance with depth that has been detected for a scene to ensure that non-specular pixels that are bright due to their close proximity to the light source and camera are not treated as specular pixels.

Other considerations not directly associated with depth information (e.g., user gaze, spatial centrality, etc.) may also be accounted for by auto-exposure algorithms described herein, as will also be described below. In these ways, the depth of foreground and background content captured in images of a scene may be better accounted for to allow users to see more detail of the content most important to them at a desirable and comfortable level of exposure.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Apparatuses, methods, and systems, described herein may provide any of the benefits mentioned above, as well as various additional and/or alternative benefits that will be described and/or made apparent below.

FIG. 1 shows an illustrative auto-exposure management apparatus 100 (apparatus 100) for depth-based auto-exposure management in accordance with principles described herein. Apparatus 100 may be implemented by computer resources (e.g., processors, memory devices, storage devices, etc.) included within an image capture system (e.g., an endoscopic or other medical imaging system, etc.), by computer resources of a computing system associated with an image capture system (e.g., communicatively coupled to the image capture system), and/or by any other suitable computing resources as may serve a particular implementation.

As shown, apparatus 100 may include, without limitation, a memory 102 and a processor 104 selectively and communicatively coupled to one another. Memory 102 and processor 104 may each include or be implemented by computer hardware that is configured to store and/or process computer instructions (e.g., software, firmware, etc.). Various other components of computer hardware and/or software not explicitly shown in FIG. 1 may also be included within apparatus 100. In some examples, memory 102 and processor 104 may be distributed between multiple devices and/or multiple locations as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause apparatus 100 to perform any of the functionality described herein. Instructions 106 may be implemented by any suitable application, software, firmware, code, script, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, or the like. Using processor 104 (e.g., when processor 104 is directed to perform operations represented by instructions 106 stored in memory 102), apparatus 100 may perform various functions associated with depth-based auto-exposure management in accordance with principles described herein.

Figure 2:
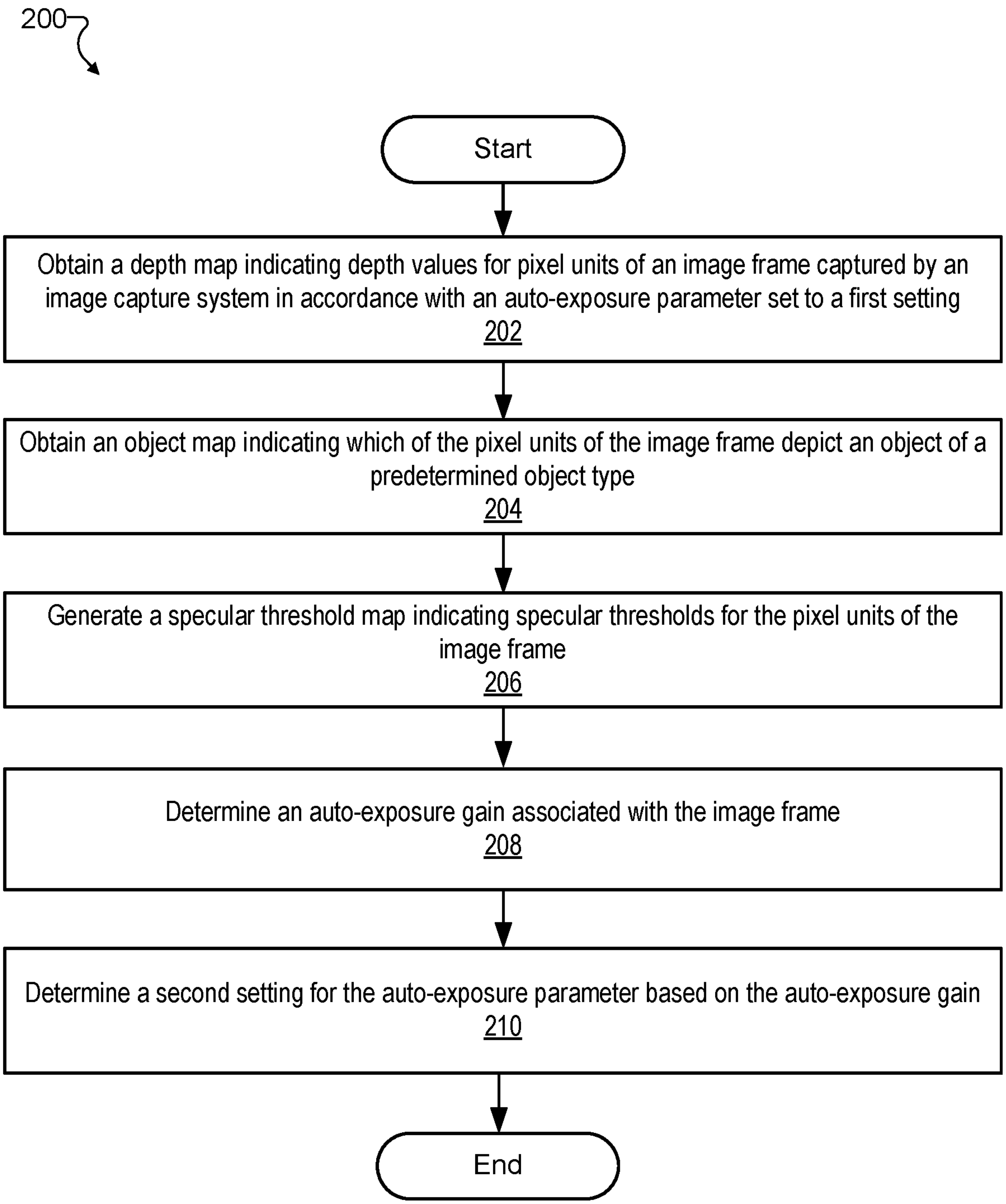
FIG. 2 shows an illustrative auto-exposure management method for depth-based auto-exposure management in accordance with principles described herein.

As one example of functionality that processor 104 may perform, FIG. 2 shows an illustrative method 200 for depth-based auto-exposure management that apparatus 100 may perform in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 or described in relation to FIG. 2 may be performed concurrently (e.g., in parallel) with one another, rather than being performed sequentially as illustrated and/or described. One or more of the operations shown in FIG. 2 may be performed by an auto-exposure management apparatus (e.g., apparatus 100), an auto-exposure management system (e.g., an implementation of an auto-exposure management system described below), and/or any implementation thereof.

In some examples, certain operations of FIG. 2 may be performed in real time so as to provide, receive, process, and/or use data described herein immediately as the data is generated, updated, changed, exchanged, or otherwise becomes available. Moreover, certain operations described herein may involve real-time data, real-time representations, real-time conditions, and/or other real-time circumstances. As used herein, real time will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time data, real-time representations, real-time conditions, and so forth, will be understood to refer to data, representations, and conditions that relate to a present moment in time or a moment in time when determinations are being made and operations are being performed (e.g., even if after a short delay), such that the data, representations, conditions, and so forth are temporally relevant to the decisions being made and/or the operations being performed.

Each of operations 202-210 of method 200 will now be described in more detail as the operations may be performed by apparatus 100 (e.g., by processor 104 as processor 104 executes instructions 106 stored in memory 102).

At operation 202, apparatus 100 may obtain a depth map corresponding to an image frame. The image frame may be captured by an image capture system in accordance with an auto-exposure parameter set to a first setting. For example, as will be described in more detail below, the auto-exposure parameter may be implemented as any of various types of parameters including an exposure time parameter (where the first setting would represent a particular amount of time that the image frame is exposed), a particular type of gain parameter (where the first setting would represent a particular amount of that type of gain that is applied to the captured image frame), an illumination intensity parameter (where the first setting would represent a particular amount of illumination that was generated by an illumination source to illuminate the scene when the image frame was captured), or another suitable auto-exposure parameter. In some examples, the image capture system may capture the image frame as part of capturing a sequence of image frames. For instance, the image frame may be one frame of a video file or streaming video captured and provided by the image capture system.

The depth map obtained at operation 202 may correspond to this image frame by indicating depth values for pixel units of the image frame. As used herein, a pixel unit may refer either to an individual picture element (pixel) comprised within an image (e.g., an image frame included in an image frame sequence) or to a group of pixels within the image. For instance, while some implementations may process images on a pixel-by-pixel basis, other implementations may divide an image into cells or groupings of pixels (e.g., 2×2 groupings, 4×4 groupings, etc.) such that processing may be performed on a cell-by-cell basis. As such, the pixel unit term will be used herein to refer to either individual pixels or groupings of pixels (e.g., pixel cells) as may be applicable for a given implementation.

As will be described in more detail below, the depth values of the obtained depth map may indicate depth information for each pixel unit of the image frame in any manner as may serve a particular implementation. For example, depth information may be represented using grayscale image data in which one extreme value (e.g., a white color value, a binary value that includes all '1's, etc.) corresponds to one extreme in depth (e.g., the highest depth value or closest that content can be to the image capture device), while another extreme value (e.g., a black color value, a binary value that includes all '0's, etc.) corresponds to the other extreme in depth (e.g., the lowest depth value or farthest that content can be to the image capture device). This depth information may be detected and generated for the image frame in any suitable way. For instance, as will be described in more detail below, a depth map may be generated based on stereoscopic differences between two versions of a particular image frame or based on other depth detection devices or techniques (e.g., devices that employ a time-of-flight or other suitable depth detection technique).

At operation 204, apparatus 100 may obtain an object map corresponding to the image frame, Just as the depth map obtained at operation 202 indicates depth values for each pixel unit, the object map obtained at operation 204 may indicate object correspondence data or other object-related information about each pixel unit. For example, the object map may indicate which of the pixel units depict an object of a predetermined object type (e.g., tissue that may be held up for examination during a medical procedure and is to be prioritized, instrumentation being used to manipulate such tissue during the medical procedure and is not to be prioritized, etc.). Similar to the depth map and as will further be described and illustrated below, the object map may represent object correspondence data in any suitable way and may determine this data to form the object map in any manner as may serve a particular implementation.

At operation 206, apparatus 100 may generate a specular threshold map corresponding to the image frame. For example, the specular threshold map may be generated based on the depth map obtained at operation 202 and, in certain examples, may also account for the object correspondence data of the object map obtained at operation 204. The specular threshold map may indicate specular thresholds for each of the pixel units of the image frame. As used herein, a specular threshold refers to a threshold of a particular characteristic (e.g., luminance, chrominance, etc.) that, when satisfied by a particular pixel unit, justifies treatment of that pixel unit as a specular pixel. As mentioned above, specular pixels may be ignored or accorded less weight by an auto-exposure algorithm because these pixels have been determined to be so bright (e.g., as a result of a glare that directly reflects a light source, etc.) as to be unrecoverable by a single exposure. Accordingly, the thresholds at which different pixel units are designated as specular pixels may significantly influence the auto-exposure management of an image frame sequence and it would be undesirable to mischaracterize a pixel unit as being an unrecoverable specular pixel unit if in fact the pixel unit is bright only as a result of being particularly close to the image capture device and the light source (e.g., because it is being held close to the camera for examination). Thus, by generating the specular threshold map based on the depth map at operation 206, such depth attributes may be properly accounted for on a pixel-unit-by-pixel-unit basis to thereby avoid such mischaracterizations.

At operation 208, apparatus 100 may determine an auto-exposure gain associated with the image frame based on the depth map obtained at operation 202, the object map obtained at operation 204, and/or the specular threshold map generated at operation 206. For example, in various implementations, apparatus 100 may account only for the depth map and the object map, only for the depth map and the specular threshold map, only for the object map and the specular threshold map, for all three of the depth, object, and specular threshold maps, or for some other suitable combination of these and/or other factors (e.g., a spatial map such as will be described in more detail below).

The auto-exposure gain for the image frame may be determined in any manner as may serve a particular implementation. For example, as will be described in more detail below, apparatus 100 may analyze the image frame to determine a weighted frame auto-exposure value and a weighted frame auto-exposure target for the image frame, then may determine the auto-exposure gain based on the weighted frame auto-exposure value and target (e.g., by computing the quotient of the auto-exposure target divided by the auto-exposure value or in another suitable way).

As used herein, an auto-exposure value will be understood to represent one or more auto-exposure-related characteristics (e.g., luminance, signal intensity, chrominance, etc.) of a particular image frame or portion thereof (e.g., pixel unit, etc.). For example, such characteristics may be detected by analyzing the image frame captured by the image capture system. A frame auto-exposure value may refer to an average luminance determined for pixel units of an entire image frame (or a designated portion thereof such as a central region that leaves out the peripheral pixel units around the edges, etc.), while a pixel auto-exposure value may refer to an average luminance determined for a pixel unit of the image frame.

It will be understood that the average luminance (and/or one or more other average exposure-related characteristics in certain examples) referred to by an auto-exposure value may be determined as any type of average as may serve a particular implementation. For instance, an auto-exposure value may refer to a mean luminance of an image frame, pixel unit, or portion thereof, determined by summing respective luminance values for each pixel or pixel unit of the frame (or portion thereof) and then dividing the sum by the total number of values. As another example, an auto-exposure value may refer to a median luminance of the image frame, pixel unit, or portion thereof, determined as the central luminance value when all the respective luminance values for each pixel or pixel unit of the frame (or portion thereof) are ordered by value. As yet another example, an auto-exposure value may refer to a mode luminance of the image frame, pixel unit, or portion thereof, determined as whichever luminance value, of all the respective luminance values for each pixel or pixel unit of the image frame (or portion thereof), is most prevalent or repeated most often. In other examples, other types of averages (besides mean, median, or mode) and other types of exposure-related characteristics (besides luminance) may also be used to determine an auto-exposure value in any manner as may serve a particular implementation.

As used herein, an auto-exposure target will be understood to refer to a target (e.g., a goal, a desirable value, an ideal, an optimal value, etc.) for the auto-exposure value of a particular image frame, pixel unit, or portion thereof. Apparatus 100 may determine the auto-exposure target, based on the particular circumstances and any suitable criteria, for the auto-exposure-related characteristics represented by the auto-exposure values. For example, auto-exposure targets may be determined at desirable levels of luminance (or other exposure-related characteristics) such as a luminance level associated with middle gray or the like. As such, a frame auto-exposure target may refer to a desired target luminance determined for pixels of an entire image frame, while a pixel auto-exposure target may refer to a desired target luminance determined for a particular pixel unit of the image frame.

In some examples, an auto-exposure target for a particular image frame or pixel unit may be determined as an average of the respective auto-exposure targets of pixels or pixel groups included within that image frame or image component. For example, similarly as described above in relation to how auto-exposure values may be averaged, a mean, median, mode, or other suitable type of auto-exposure target average may be computed to determine an auto-exposure target for an image frame, pixel unit, or portion thereof.

The auto-exposure gain determined at operation 208 may correspond to a ratio of an auto-exposure target to an auto-exposure value of the image frame, each of which may be determined in a manner that weights the data from the depth, object, and/or specular threshold maps in any of the ways described herein. In this way, if the auto-exposure value for the image frame is already equal to the auto-exposure target for the image frame (e.g., such that no further adjustment is needed to align to the target), the determined auto-exposure gain may be set to a gain of 1, so that the system will neither try to boost nor attenuate the auto-exposure values for subsequent image frames to be captured by the image capture system. Conversely, if the frame auto-exposure target is different from the frame auto-exposure value, the determined auto-exposure gain may be set to correspond to a value less than or greater than 1 to cause the system to adjust auto-exposure parameters in a manner configured to either boost or attenuate the auto-exposure values for the subsequent frames. In this way, apparatus 100 may attempt to make the auto-exposure values for the subsequent frames more closely align with the desired auto-exposure target.

At operation 210, apparatus 100 may determine a second setting for the auto-exposure parameter (e.g., the same auto-exposure parameter referred to above with respect to the first setting that was used to capture the image frame). This second setting for the auto-exposure parameter may be configured to be used by the image capture system to capture one or more subsequent image frames (e.g., later image frames in the sequence of image frames being captured by the image capture system). For example, the second setting may be a slightly longer or shorter exposure time to which an exposure time parameter is to be set, a slightly higher or lower gain to which a particular gain parameter is to be set, or the like.

The determining of the second setting at operation 210 may be performed based on the auto-exposure gain determined at operation 208. In this way, auto-exposure management will not only account for the depth of foreground and background content, but may do so in a way that distinguishes different types of content (e.g., tissue content that is to be prioritized, instrument objects that are not to be prioritized, etc.). As will be further described below, additional operations may follow operation 210, such as updating the auto-exposure parameter to reflect the second setting determined at operation 210, obtaining and processing subsequent image frames, and so forth.

Apparatus 100 may be implemented by one or more computing devices or by computing resources of a general purpose or special purpose computing system such as will be described in more detail below. In certain embodiments, the one or more computing devices or computing resources implementing apparatus 100 may be communicatively coupled with other components such as an image capture system used to capture the image frames that apparatus 100 processes. In other embodiments, apparatus 100 may be included within (e.g., implemented as a part of) an auto-exposure management system. Such an auto-exposure management system may be configured to perform all the same functions described herein to be performed by apparatus 100 (e.g., including some or all of the operations of method 200, described above), but may further incorporate additional components such as the image capture system so as to also be able to perform the functionality associated with these additional components.

Figure 3:
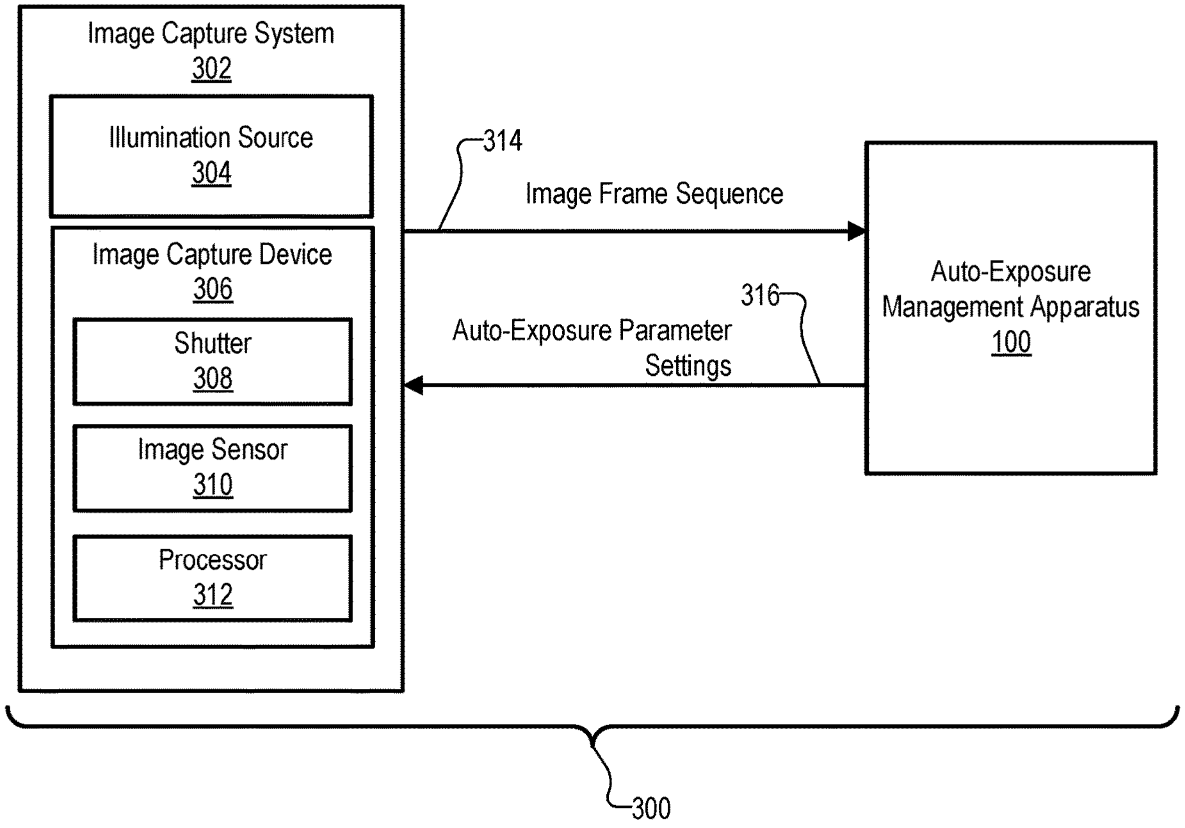
FIG. 3 shows an illustrative auto-exposure management system for depth-based auto-exposure management in accordance with principles described herein.

To illustrate, FIG. 3 shows an illustrative auto-exposure management system 300 (system 300) for depth-based auto-exposure management in accordance with principles described herein. As shown, system 300 may include an implementation of apparatus 100 together with an image capture system 302 that includes at least one illumination source 304 and an image capture device 306 that incorporates a shutter 308, an image sensor 310, and a processor 312 (e.g., one or more image signal processors implementing an image signal processing pipeline). Within system 300, apparatus 100 and image capture system 302 may be communicatively coupled to allow image capture system 302 to capture and provide an image frame sequence 314 and/or other suitable captured image data, as well as to allow apparatus 100 to direct image capture system 302 in accordance with operations described herein (e.g., to provide updates to various auto-exposure parameter settings 316). Image capture system 302 will now be described.

Illumination source 304 may be implemented by any source of visible or other light (e.g., visible light, fluorescence excitation light such as near-infrared light, etc.) and may be configured to interoperate with image capture device 306 within image capture system 302. Illumination source 304 may be configured to emit light to, for example, illuminate tissue within a body (e.g., a body of a live animal, a human or animal cadaver, a portion of human or animal anatomy, tissue removed from human or animal anatomies, non-tissue work pieces, training models, etc.) with visible illumination during a performance of a medical procedure (e.g., a surgical procedure, etc.). In some examples, illumination source 304 (or a second illumination source not explicitly shown) may be configured to emit non-visible light to illuminate tissue to which a fluorescence imaging agent (e.g., a particular dye or protein, etc.) has been introduced (e.g., injected) so as to cause fluorescence in the tissue as the body undergoes a fluorescence-guided medical procedure.

Image capture device 306 may be configured to capture image frames in accordance with one or more auto-exposure parameters that are set to whatever auto-exposure parameter settings 316 are directed by apparatus 100. Image capture device 306 may be implemented by any suitable camera or other device configured to capture images of a scene. For instance, in a medical procedure example, image capture device 306 may be implemented by an endoscopic imaging device configured to capture image frame sequence 314, which may include image frames (e.g., stereoscopic image frames) depicting an internal view of the body that features the tissue illuminated by illumination source 304. As shown, image capture device 306 may include components such as shutter 308, image sensor 310, and processor 312.

Image sensor 310 may be implemented by any suitable image sensor, such as a charge coupled device (CCD) image sensor, a complementary metal-oxide semiconductor (CMOS) image sensor, or the like.

Shutter 308 may interoperate with image sensor 310 to assist with the capture and detection of light from the scene. For example, shutter 308 may be configured to expose image sensor 310 to a certain amount of light for each image frame captured. Shutter 308 may comprise an electronic shutter and/or a mechanical shutter. Shutter 308 may control how much light image sensor 310 is exposed to by opening to a certain aperture size defined by a shutter aperture parameter and/or for a specified amount of time defined by an exposure time parameter. As will be described in more detail below, these or other shutter-related parameters may be included among the auto-exposure parameters that apparatus 100 is configured to determine, update, and adjust.

Processor 312 may be implemented by one or more image signal processors configured to implement at least part of an image signal processing pipeline. Processor 312 may process auto-exposure statistics input (e.g., by tapping the signal in the middle of the pipeline to detect and process various auto-exposure data points and/or other statistics), perform optics artifact correction for data captured by image sensor 310 (e.g., by reducing fixed pattern noise, correcting defective pixels, correcting lens shading issues, etc.), perform signal reconstruction operations (e.g., white balance operations, demosaic and color correction operations, etc.), apply image signal analog and/or digital gains, and/or perform any other functions as may serve a particular implementation. Various auto-exposure parameters may dictate how the functionality of processor 312 is to be performed.

For example, auto-exposure parameters may be set to define the analog and/or digital gains processor 312 applies, as will be described in more detail below.

In some examples, an endoscopic implementation of image capture device 306 may include a stereoscopic endoscope that includes two full sets of image capture components (e.g., two shutters 308, two image sensors 310, etc.) to accommodate stereoscopic differences presented to the two eyes (e.g., left eye and right eye) of a viewer of the captured image frames. As mentioned above, depth information may be derived from differences between corresponding images captured stereoscopically by this type of image capture device. Conversely, in other examples, an endoscopic implementation of image capture device 306 may include a monoscopic endoscope with a single shutter 308, a single image sensor 310, and so forth. In this example, depth information used for the depth map may be determined by way of another technique (e.g., using a time-of-flight device or other depth capture device or technique).

Apparatus 100 may be configured to control the settings 316 for various auto-exposure parameters of image capture system 302. As such, apparatus 100 may adjust and update settings 316 for these auto-exposure parameters in real time based on incoming image data (e.g., image frame sequence 314) captured by image capture system 302. As mentioned above, certain auto-exposure parameters of image capture system 302 may be associated with shutter 308 and/or image sensor 310. For example, apparatus 100 may direct shutter 308 in accordance with an exposure time parameter corresponding to how long the shutter is to allow image sensor 310 to be exposed to the scene, a shutter aperture parameter corresponding to an aperture size of the shutter, or any other suitable auto-exposure parameters associated with the shutter. Other auto-exposure parameters may be associated with aspects of image capture system 302 or the image capture process unrelated to shutter 308 and/or sensor 310. For example, apparatus 100 may adjust an illumination intensity parameter of illumination source 304 that corresponds to an intensity of illumination provided by illumination source 304, an illumination duration parameter corresponding to a time period during which illumination is provided by illumination source 304, or the like. As another example, apparatus 100 may adjust gain parameters corresponding to one or more analog and/or digital gains (e.g., an analog gain parameter, a Bayer gain parameter, an RGB gain parameter, etc.) applied by processor 312 to luminance data generated by image sensor 310.

Any of these or other suitable parameters, or any combination thereof, may be updated and/or otherwise adjusted by apparatus 100 for subsequent image frames based on an analysis of the current image frame. For instance, in one example where the auto-exposure gain is determined to be 6.0, various auto-exposure parameters could be set as follows: 1) a current illumination intensity parameter may be set to 100% (e.g., maximum output); 2) an exposure time parameter may be set to $1/60^{th}$ of a second (e.g., 60 fps); 3) an analog gain may be set to 5.0 (with a cap of 10.0); 4) a Bayer gain may be set to 1.0 (with a cap of 3.0); and 5) an RGB gain may be set to 2.0 (with a cap of 2.0). With these settings, the gain is distributed across the analog gain (10.0/5.0=2.0), Bayer gain (3.0/1.0=3.0), and RGB gain (2.0/2.0=1.0) to establish the desired 6.0 total auto-exposure gain (3.0*2.0*1.0=6.0) for the frame.

The timing at which parameters are changed may be applied by system 300 with care so as to adjust auto-exposure effects gradually and without abrupt and/or noticeable changes. For example, even if apparatus 100 determines that a relatively large update is called for with respect to a particular auto-exposure parameter setting, the setting may be changed slowly over a period of time (e.g., over the course of several seconds, etc.) or in stages (e.g., frame by frame) so as not to create a jittery and undesirable effect to be perceived by the user, as well as to avoid responding too quickly to outlier data that may not actually represent the most desirable settings for the auto-exposure parameters.

Figure 4:
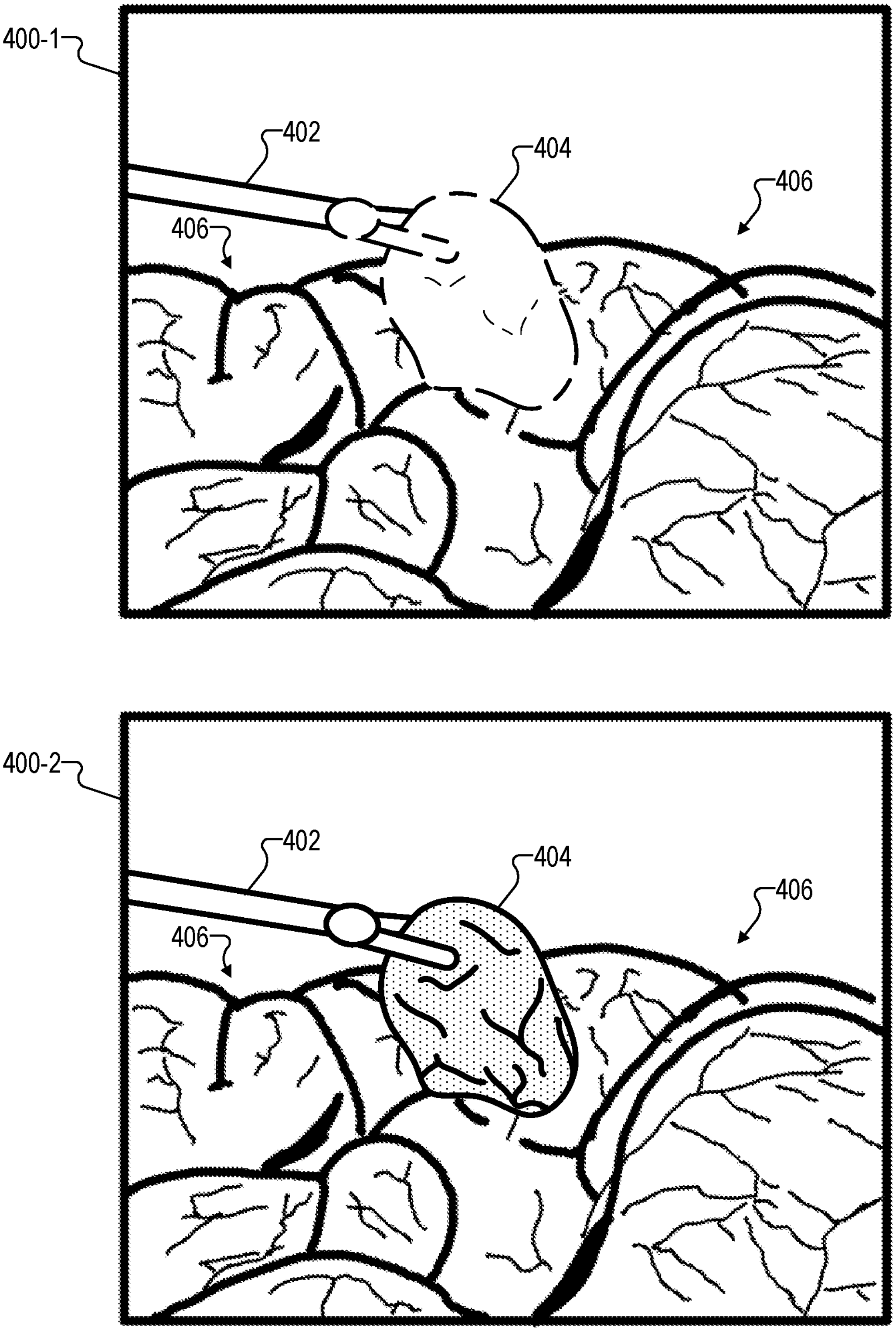
FIG. 4 shows image frames that illustrate the results of applying depth-based auto-exposure management principles described herein.

FIG. 4 shows two different image frames 400, labeled as image frames 400-1 and 400-2, that illustrate the results of applying depth-based auto-exposure management principles described herein. Specifically, image frame 400-1 illustrates an image frame in which auto-exposure management is performed in a conventional manner that does not account for depth differences of foreground elements and background elements, while image frame 400-2 illustrates an image frame in which depth-based auto-exposure management is performed in accordance with principles described herein so as to account for the depth difference in various ways (e.g., distinguishing different types of objects, using custom specular thresholds for different content rather than a static global specular threshold for the entire frame, etc.).

As shown, each image frame 400 in FIG. 4 depicts an instrument 402 that is holding a tissue sample 404 close to the image capture device such that tissue sample 404 may be more closely examined by a user viewing the image frame. In this example, instrument 402 is shown to be a tissue manipulation instrument that may be controlled by a computer-assisted medical system such as will be described in more detail below. While tissue sample 404 shown in the image frames 400 of FIG. 4 is shown to be a piece of tissue that appears to be detached from other anatomy at the scene depicted in the image frames, it will be understood that the tissue sample held up for examination, instead of being a detached piece of tissue, may be a segment of tissue or other anatomy that is still attached to other anatomy of the body. In other examples, an object of interest held close to the image capture device for examination may not be anatomical, but may be another object such as a suturing needle or other such tool or, in non-medical examples, may be any other type of object as may serve a particular implementation. In any case, while instrument 402 and tissue sample 404 (also referred to as foreground objects 402 and 404) are shown in image frames 400 to be foreground content relatively close to the image capture device capturing the image frames, other tissue and anatomical structures not actively held up to the image capture device are labeled as background content 406 in both image frames 400 of FIG. 4.

In image frame 400-1, FIG. 4 shows that foreground objects 402 and 404 are overexposed such that it is difficult to see certain details of the objects. This is shown in FIG. 4 by thin, disjointed lines outlining these objects and few details (e.g., folds, vasculature, etc.) being discernable on tissue sample 404. In contrast, in image frame 400-2, FIG. 4 shows that auto-exposure management for foreground objects 402 and 404 is performed in a way that accounts for the depth characteristics of these objects such that significantly more detail can be appreciated in the depiction. This is shown in FIG. 4 by thicker lines outlining these objects, additional details becoming discernable, and a darker tone (indicated by dots) being shown for tissue sample 404. In both examples, auto-exposure management of background content 406, which is less susceptible to depth-based issues than foreground objects 402 and 404, is shown to be performed in a manner that allows a high level of detail to be seen for this content. However, it will be understood that, to the extent that auto-exposure parameters cannot be found that provide suitable auto-exposure management for all the content at the scene, depth-based auto-exposure algorithms described herein to output image frame 400-2 may cause foreground objects of interest (e.g., tissue sample 404 in this example) to be prioritized over background content, rather than the background being prioritized over the objects of interest in the foreground (as shown by image frame 400-1 output from the conventional auto-exposure algorithm).

Figure 5:
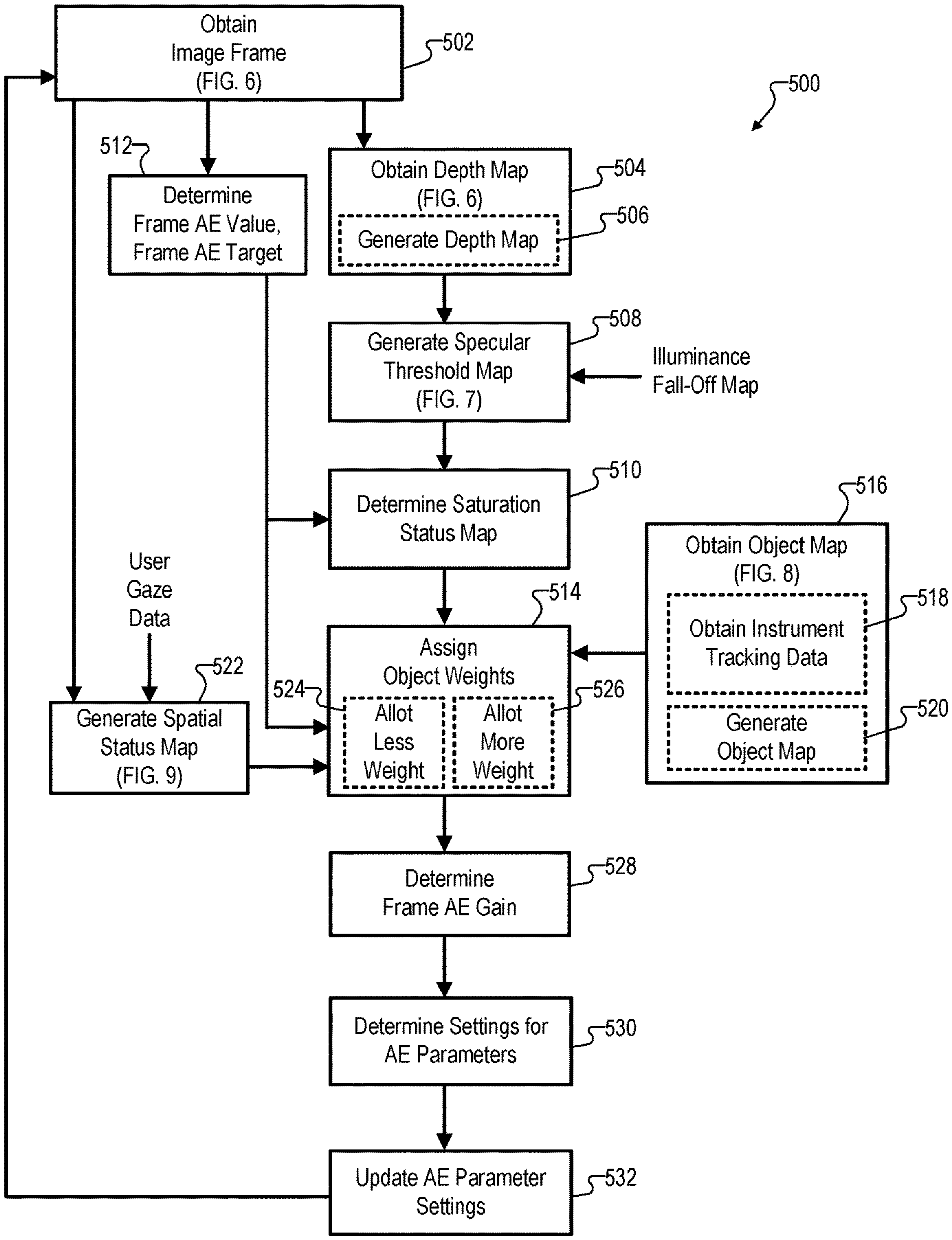
FIG. 5 shows an illustrative flow diagram for depth-based auto-exposure management in accordance with principles described herein.

FIG. 5 shows an illustrative flow diagram 500 for depth-based auto-exposure management using, for example, an implementation of apparatus 100, method 200, and/or system 300. As shown, flow diagram 500 illustrates various operations 502-532, which will each be described in more detail below. It will be understood that operations 502-532 represent one embodiment of depth-based auto-exposure management, and that other embodiments may omit, add to, reorder, and/or modify any of these operations. For example, while flow diagram 500 shows depth-based auto-exposure management based on a depth map, a specular threshold map, and an object map, alternative implementations will be illustrated and described below in relation to FIGS. 10 and 11 that perform depth-based auto-exposure management based on different sets of information than that utilized in the example of flow diagram 500.

As will be described, various operations 502-532 of flow diagram 500 may be performed for one image frame or multiple image frames (e.g., each image frame in an image frame sequence). It will be understood that, depending on various conditions, not every operation might be performed for every image frame, and the combination and/or order of operations performed from frame to frame in the image frame sequence may vary. Operations 502-532 of flow diagram 500 will now be described in relation to FIG. 5 and with further reference to FIGS. 6-9, as indicated for certain operations in FIG. 5.

Figure 6:
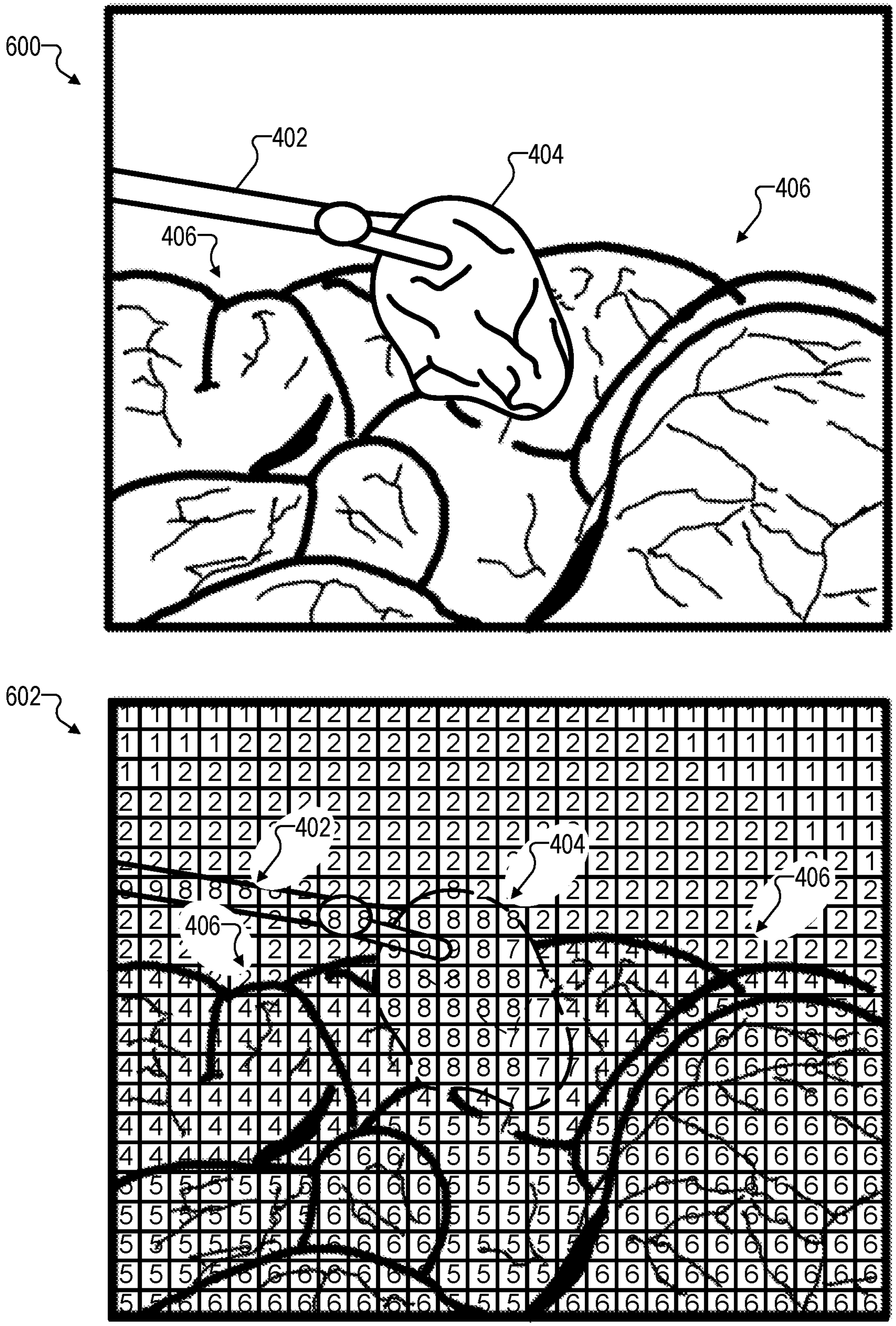
FIG. 6 shows an illustrative image frame and a depth map corresponding to the image frame in accordance with principles described herein.

At operation 502, apparatus 100 may obtain an image frame. For example, as described above, the image frame may be captured by an image capture system (e.g., image capture system 302) in accordance with one or more auto-exposure parameters that are set to particular settings and that may be reevaluated and adjusted based on the image frame in the ways described below. To illustrate, FIG. 6 shows an image frame 600 depicting an example scene similar to the medical procedure scene described above in relation to FIG. 4. Specifically, as shown, the scene depicted in image frame 600 includes instrument 402, which is holding tissue sample 404 in front of background content 406 in order that a user (e.g., a surgeon) viewing image frame 600 may be enabled to closely examine tissue sample 404. It is noted that auto-exposure for image frame 600 is drawn to be neither as overexposed as illustrated above for image frame 400-1, nor as optimally exposed as image frame 400-2. In this way, image frame 600 illustrates that image frames captured by depth-based auto-exposure systems described herein may use parameter settings that are superior to settings produced by conventional algorithms but that are still being adjusted and improved from frame to frame (e.g., based on the analysis of image frame 600 performed by flow diagram 500).

Returning to FIG. 5, at operation 504, apparatus 100 may obtain a depth map corresponding to the image frame obtained at operation 502 (e.g., corresponding to image frame 600). In some examples, the depth map obtained at operation 504 may be generated by a system or process independent from apparatus 100 such that apparatus 100 may obtain the depth map by accessing or receiving the depth map from an external source. For example, the image capture system capturing and providing image frame 600 may further be configured to capture and/or generate a depth map for image frame 600 and to provide the depth map together with the image frame itself. In other examples, an operation 506 (drawn with a dotted line to indicate that this operation is optional and represents just one illustrative way that operation 504 may be accomplished) may be performed in which, based on the obtained image frame 600, apparatus 100 itself generates the depth map.

The generation of the depth map at operation 506 may be performed in any suitable way. For instance, in certain examples the image capture system providing image frame 600 may be a stereoscopic image capture system and image frame 600 may be a stereoscopic image frame that includes a left-side version and a right-side version of the image frame. In this scenario, the obtaining the depth map corresponding to image frame 600 at operation 506 may include generating the depth map based on differences between corresponding features that are depicted in both the left-side and right-side versions of the image frame. For example, apparatus 100 may identify corresponding features (e.g., pixels or groups of pixels depicting the same corners, edges, ridges, etc., of the scene content) and use triangulation techniques (e.g., based on a known distance and angle relationship between left-side and right-side image capture devices capturing the respective left-side and right-side versions of the image frame) to compute the depths of each of these features.

To illustrate, FIG. 6 also shows, along with image frame 600, an illustrative depth map 602 that is associated with image frame 600 (e.g., by indicating depth values for pixel units of image frame 600). As shown, depth map 602 overlays a grid of numbered boxes onto the imagery of image frame 600 to clearly show how depth data corresponds to different parts of the image. In depth map 602, each numbered box represents a depth value for a particular pixel unit of image frame 600, such as a single pixel or a grouping of pixels in a cell that the image frame may be divided into. While an arbitrary one-digit depth representation is used for depth map 602, it will be understood that the depth values in a given implementation of a depth map may be represented in any suitable way to provide more convenient and accurate information at any suitable level of resolution as may serve a particular implementation. For instance, rather than a one-digit base-10 value as is used for convenience in FIG. 6, one implementation may employ 16-bit, 32-bit, or other suitably-sized binary values for each depth value of the depth map. In the illustrated depth representation, it will be understood that lower numbers represent greater depths (e.g., surfaces that are relatively far away from the vantage point of the image capture device) while higher values represent smaller depths (e.g., surfaces that are relatively proximate to the vantage point of the image capture device). As such, for example, depth map 602 illustrates that instrument 402 and tissue sample 404 are relatively close to the image capture device (e.g., having relatively high depth values from approximately 7-9), certain background content 406 are less proximate to the image capture device (e.g., having lower depth values from approximately 4-6), and other background content is even less proximate to the image capture device (e.g., having depth values of 1-2).

As mentioned above, stereoscopic depth detection techniques are just one possible type of depth detection technique that may be employed to generate a depth map such as depth map 602. Additionally or alternatively, other types of techniques such as involving time-of-flight imaging may be used together with, or in place of, the stereoscopic depth detection techniques. Regardless of the depth detection technique employed in a given implementation, the determination of depth values will be understood to be a process that can potentially be prone to imprecision or inaccuracy for various reasons, especially when performed in real time. Accordingly, in certain examples, a depth map such as depth map 602 may be made to include, for each pixel unit represented in the depth map, both a depth value (shown in depth map 602 as the single-digit values in the boxes) and a confidence value associated with the depth value (not explicitly shown in depth map 602). For example, each confidence value may indicate a measure of how reliable the corresponding estimated depth value is likely to be for that pixel unit based on various considerations (e.g., how closely the corresponding feature matched between the versions of image frame 600, the angle of the feature with respect to the vantage point of the image capture device, etc.). In implementations employing confidence values of this type, it will be understood that the weighting and other operations associated with determining an auto-exposure gain (described in more detail below) may be based on both the depth values and the confidence values included in the depth map.

Returning to FIG. 5, at operation 508, apparatus 100 may generate a specular threshold map corresponding to the image frame obtained at operation 502 (e.g., corresponding to image frame 600). Specifically, the specular threshold map may be generated based on the depth map obtained at operation 504 (e.g., depth map 602) and may indicate specular thresholds for the pixel units of the image frame. As will be described in more detail below, the auto-exposure gain associated with image frame 600 may be further based on the specular threshold map generated at operation 508 (along with being based on depth values and confidence values described above and other information that will be described in more detail).

As mentioned above, a specular threshold for a given pixel unit refers to a threshold auto-exposure value (e.g., a threshold of illuminance, brightness, signal intensity, or another such pixel unit characteristic) that, when satisfied, indicates that the pixel unit is to be treated as a specular pixel unit. Specular pixel units are those that have been determined to have characteristics so extreme as to not be unrecoverable or otherwise not worth attempting to fully account for in auto-exposure management processing. For instance, specular pixel units may reflect light directly from the light source and may appear as a white area of glare on an object. Because these pixels have such high brightness or intensity, they are likely to saturate no matter how auto-exposure parameter settings are adjusted (or unless settings are adjusted in an extreme way that would severely underexpose the remainder of the content). Accordingly, a productive strategy for handling auto-exposure management of these pixels is to ignore or at least heavily discount them so that they do not significantly influence the frame auto-exposure value in a way that does not actually represent how desirably exposed the rest of the content in the image frame is.

While conventional auto-exposure management strategies may set a static specular threshold value, depth-based auto-exposure management strategies described herein may generate a specular threshold map such that each pixel unit is assigned an appropriate specular threshold that accounts for its depth (e.g., its distance from the light source and the image capture device, etc.). In this way, pixel units depicting an object such as tissue sample 404 being intentionally held up to the camera for examination (e.g., and, as a consequence, also held more proximate to the light source) may receive more accurate specular pixel unit designations because this proximity to the light can be accounted for. For example, there may be a much lower incidence of false positives identified in which pixel units that are not specular pixels units (and that, thus, should influence auto-exposure parameter settings) are designated as being specular pixel units merely as a result of being closer to the light source.

Apparatus 100 may generate the specular threshold map at operation 508 in any suitable way and based on any suitable information. For example, as shown, the specular threshold map may be based at least in part on depth map 602 generated at operation 504. Higher depth values (e.g., depth values indicating more proximity to the light source and image capture device) for certain pixel units may, for instance, cause corresponding specular thresholds for those pixel units to also be higher so as to avoid the false positive designations described above. Additionally, as further shown in FIG. 5, the generating of the specular threshold map at operation 508 may be further based on an illuminance fall-off map that indicates how illuminance within a scene depicted by image frame 600 decreases as a function of distance from the illumination source. For example, the illuminance fall-off map may encode pre-calibrated information about the illumination source, how bright the light is that originates from this light source, the inverse square law dictating how the light intensity naturally diminishes with distance from the light source, and so forth. Based on this information and/or any other suitable information not explicitly shown in FIG. 5, operation 508 may be performed to generate a specular threshold map that assigns customized specular threshold values to each pixel unit based on their depth and the lighting conditions of the scene.

Figure 7:
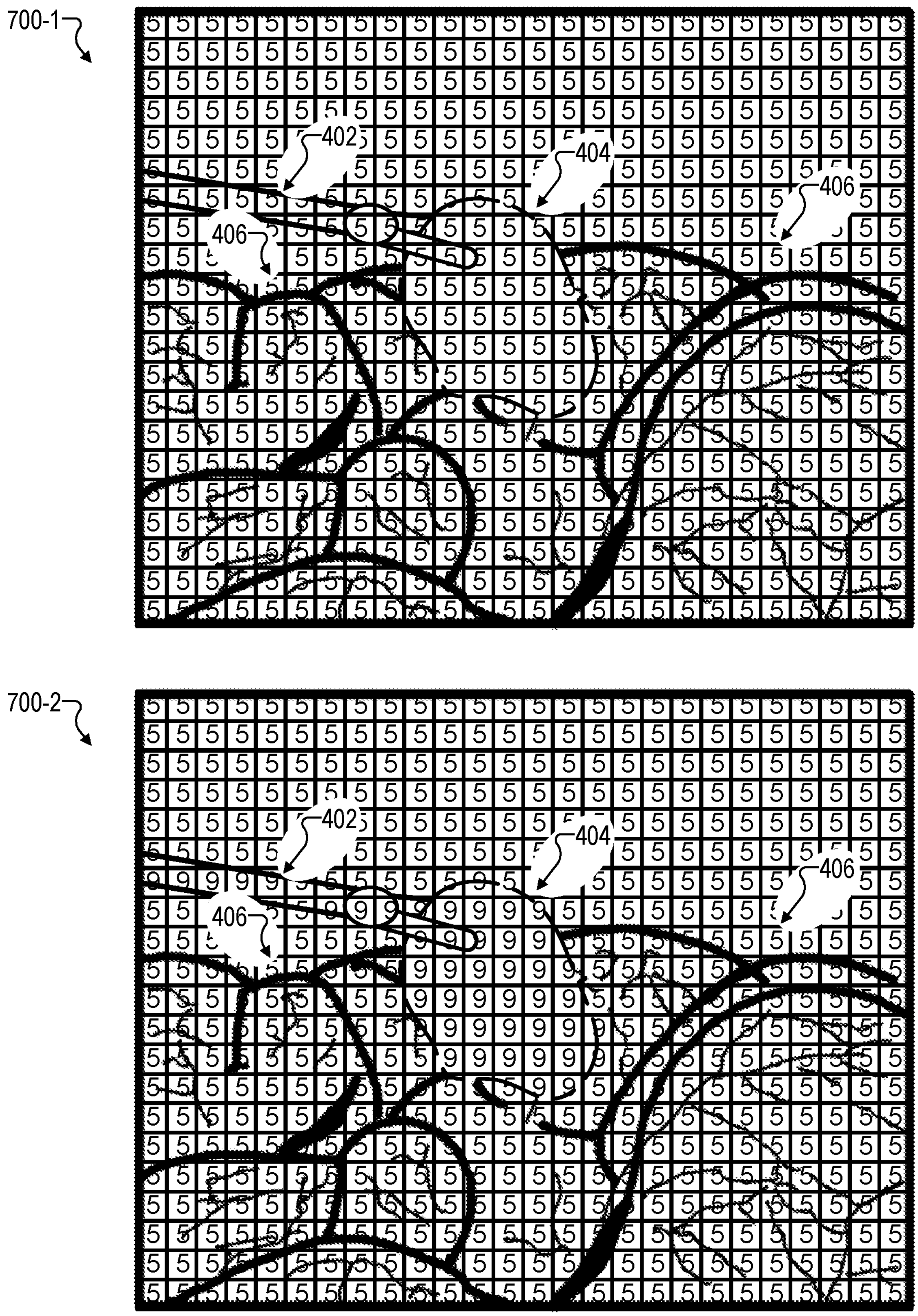
FIG. 7 shows two illustrative specular threshold maps corresponding to the image frame of FIG. 6 in accordance with principles described herein.

To illustrate, FIG. 7 shows two illustrative specular threshold maps 700 (e.g., specular threshold maps 700-1 and 700-2) that each correspond to image frame 600. As shown, specular threshold maps 700 are similar in format to depth map 602 in that they are depicted using a grid of small boxes (representing the various pixel units of the image frame) overlayed onto the imagery of image frame 600 and each including a single-digit value. However, in this case, rather than representing depth values, the single-digit values in FIG. 7 will be understood to represent specular threshold values. For example, higher digits will be understood to represent higher thresholds (e.g., thus requiring these pixel units to have higher auto-exposure values before being designated as specular pixel units), while lower digits will be understood to represent lower thresholds (e.g., thus setting a lower bar for these pixel units to be designated as specular pixel units). The one-digit values shown in FIG. 7 will be understood to be arbitrary illustrative values that are relative to other values shown in the figure and that may correspond to specular threshold values in a given implementation in any suitable way.

In the context of the endoscopic image capture device capturing the internal imagery (e.g., imagery depicting the tissue sample 404 that is more proximate to the endoscopic image capture device than is other content 406 at the scene due to being held up for closer examination), specular threshold map 700-1 shows how specular threshold values may conventionally be mapped to pixel units of an image frame. Specifically, as shown, each specular threshold value of specular threshold map 700-1 is shown to be the same constant value (digit ‘5’) to indicate that all pixel units are treated equally regardless of their depth, their proximity to an illumination source, or any other such circumstances.

In contrast, specular threshold map 700-2 shows how specular threshold values may be mapped to pixel units of an image frame in certain depth-based auto-exposure algorithms such as illustrated by flow diagram 500. Specifically, as shown, apparatus 100 may generate the specular threshold map in a manner that allots a higher specular threshold to pixel units corresponding to the tissue sample 404 than to pixel units corresponding to the other content (e.g., background content 406) at the scene. In specular threshold map 700-2, it is shown that, while pixel units associated with background content 406 are all treated alike in terms of specular analysis (e.g., all background pixel units being assigned the same specular threshold value of '5'), foreground objects with significantly different depth are treated differently. As shown, for instance, instrument 402 and tissue sample 404 are allotted higher specular threshold values of '9' in this example to thereby set the bar significantly higher for specular pixels to be designated from this content (in recognition that these close-up objects are likely to be much brighter than the background content as a result of their proximity to the light source and image capture device).

While only two specular threshold values ('5' and '9') are shown in specular threshold map 700-2 to represent, essentially, background content ('5') and foreground content ('9'), it will be understood that, in other implementations, a specular threshold map may be highly nuanced with many different specular threshold values configured to reflect the realities of the depth attributes of the scene (as indicated by the depth map), illumination intensity fall-off at the scene (as indicated by the illumination fall-off map), and any other information as may serve a particular implementation.

Returning to FIG. 5, at operation 510, apparatus 100 may determine a saturation status map for the image frame based on the specular threshold map generated at operation 508 (e.g., specular threshold map 700-2), as well as based on pixel unit auto-exposure values and/or targets determined at operation 512. The saturation status map determined at operation 510 may indicate, for each pixel unit, whether an auto-exposure value for the pixel unit satisfies (e.g. exceeds) a specular threshold for the pixel unit according to the specular threshold map. In this way, the saturation status map may indicate whether each pixel unit is determined to be unrecoverably saturated, or, in other words, whether that pixel unit is designated as a specular pixel.

As mentioned, at operation 512, apparatus 100 may determine auto-exposure values and auto-exposure targets based on image frame data obtained at operation 502. For example, auto-exposure values and/or targets for each pixel unit may be determined and used by other operations such as operation 510 (described above). Additionally, a frame auto-exposure value and a frame auto-exposure target may be determined by this operation that, after being adjusted by various weightings as will be described, may be used in determining the frame auto-exposure gain that will form the basis for adjusting auto-exposure parameter settings for subsequent image frame.

At operation 514, apparatus 100 may assign weights to each pixel unit to thereby adjust the auto-exposure values and auto-exposure targets of the pixel units based on various factors, and to thereby influence the overall frame auto-exposure value and target that will be used to determine the frame auto-exposure gain. As shown, the various factors that may be accounted for in this weighting operation include the saturation status map determined at operation 510 (which may itself incorporate data from depth map 602 obtained at operation 504, specular threshold map 700-2 generated at operation 508, an illuminance fall-off map, pixel auto-exposure values determined at operation 512, and so forth as has been described), as well as other information as may serve a particular implementation (e.g., depth map 602). In this example, operation 514 is shown to also account for an object map that is obtained at an operation 516 (including optional operations 518 and 520 as will be further detailed below), as well as a spatial status map that is generated at an operation 522. Based on these various inputs and any other information as may serve a particular implementation, operation 514 may adjust auto-exposure values and/or targets for each pixel unit in a manner that accounts for the various specular-based, object-based, spatial-based, and other attributes of the pixel units to create a weighted frame auto-exposure value and target that account for these attributes in a manner that helps achieve the desired outcome of image frame 400-2.

At operation 516, apparatus 100 may obtain an object map that may be accounted for together with the depth map and saturation status map information as pixel weighting is performed at operation 514. As has been described, in certain examples, it may be desirable to distinguish depicted content not only based on its depth but also based on object type. For example, referring to image frame 600, it may be desirable to allot more weight to pixel units depicting tissue sample 404 to ensure that subsequent image frames provide desirable auto-exposure for a user to examine the tissue sample, but it may not be desirable to prioritize other proximate foreground content such as instrument 402 in this same way (since it is less likely that the user wishes to closely examine instrument 402). Accordingly, an object map obtained at operation 516 may provide information indicating which pixel units depict which types of objects such that the weighting of operation 514 may fully account for these different types of objects.

In certain examples (e.g., in certain implementations, under certain circumstances, etc.), one predetermined object type may be tissue of the body, such that an object represented by the object map obtained at operation 516 may be a tissue sample (e.g., tissue sample 404) from the body that is more proximate to the endoscopic image capture device than is other content (e.g., background content) at the scene. In other examples, a predetermined object type may be instrumentation for tissue manipulation, such that the object represented by the object map may be an instrument (e.g., instrument 402) at the scene that is more proximate to the endoscopic image capture device than is other content (e.g., background content) at the scene.

Regardless of the object type or types being tracked and represented by the object map, the object may be obtained in any suitable way. For instance, as described above for the depth map obtained at operation 504, the object map may in certain implementations be generated independently from apparatus 100 and obtained at operation 516 by accessing or receiving the object map as it has already been generated. Conversely, in other implementations, apparatus 100 may obtain the object map by performing optional operations 518-520 based on raw data obtained from other systems (e.g., from image capture system 302 or the like). For instance, if the object type being tracked is instrumentation in one example, apparatus 100 may obtain instrument tracking data at operation 518, and may generate the object map based on this instrument tracking data at operation 520. Instrument tracking data may be obtained from any suitable source (e.g., image capture system 302, a computer-assisted medical system such as will be described below, etc.), and may be identified or determined in any suitable way. As one example, the instrument tracking data may be based on kinematic parameters used to control instrument 402 at the scene. These kinematic parameters may be obtained from a computer-assisted medical system that is controlling instrument 402 using the kinematic parameters, as will be described in more detail below. As another example, the instrument tracking data may be based on computer-vision tracking of instrument 402 and may be obtained from a computer-assisted medical system performing the computer-vision tracking of the instrument (e.g., a tracking system receiving image frame sequence 314 from image capture system 302). In other examples, if the object type being tracked is tissue of the body, tissue tracking data may be generated and obtained based on computer-vision tracking or other suitable techniques analogous to those described for operation 518. At operation 520, the tracking data may be used to generate the object map that is provided to weighting operation 514.

Figure 8:
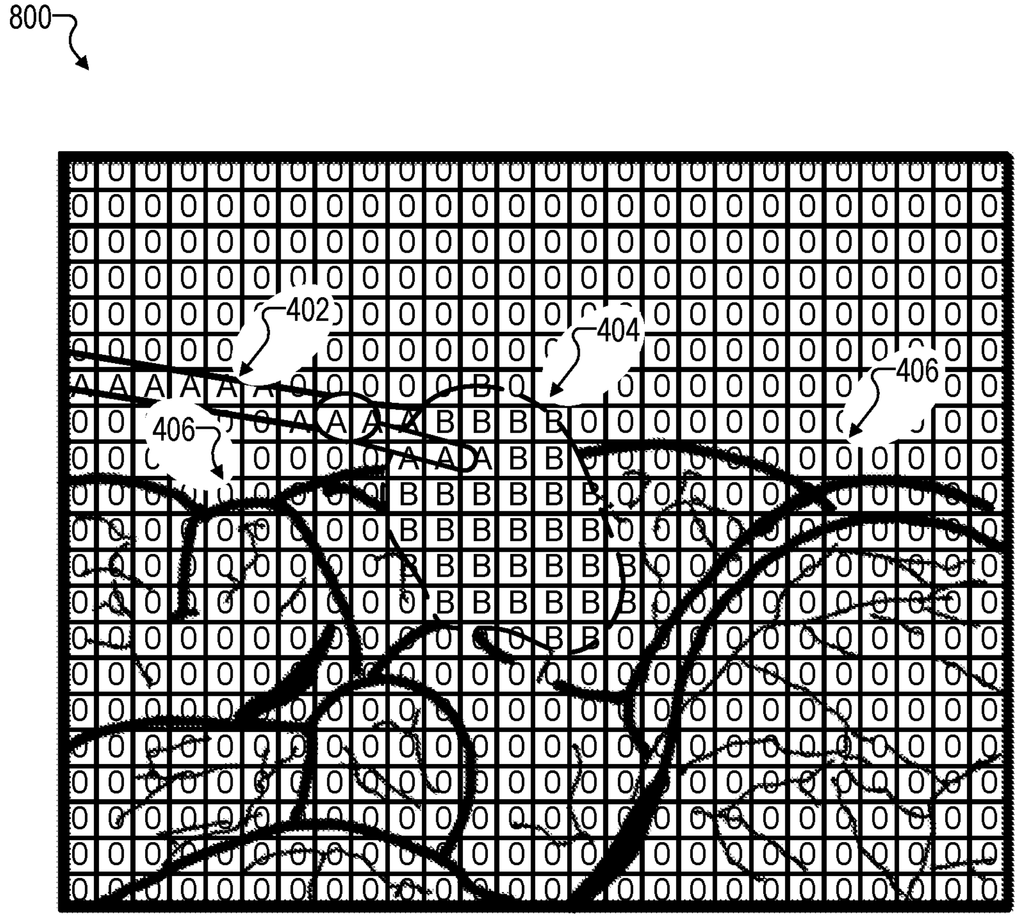
FIG. 8 shows an illustrative object map corresponding to the image frame of FIG. 6 in accordance with principles described herein.

FIG. 8 shows an illustrative object map 800 that corresponds to image frame 600 and may be obtained (e.g., and in certain examples generated) at operation 516. Similar to other data maps illustrated above, object map 800 is shown to include a grid of small boxes corresponding to the various pixel units making up image frame 600, and these boxes are overlaid for reference onto the imagery of image frame 600. However, rather than single-digit numbers representing values on a depth or specular value threshold, the boxes of object map 800 are shown to each indicate an 'A' for pixel units determined to be associated with instrument 402, a 'B' for pixel units determined to be associated with tissue sample 404, and a '0' for other pixel units that do not depict either of these objects. Based on these object designations, weighting at operation 514 may be performed in a manner that emphasizes (e.g., allots more weight to) pixel units associated with tissue sample 404, deemphasizes (e.g., allots less weight to) pixel units associated with instrument 402, and gives no special treatment (e.g., neither emphasizing nor deemphasizing) other pixel units that are not associated with these identified foreground objects.

As described above with respect to the depth map generated at operation 504, it will be understood that object recognition and tracking performed as part of generating the object map obtained at operation 516 may be inexact and imprecise by nature. As such, just as with the depth values described above, confidence values (not explicitly shown in FIG. 8) may be generated and provided together with the object correspondence values making up object map 800. In this way, apparatus 100 may have a measure of how reliable each object correspondence value in object map 800 is likely to be, and these confidence values (like the confidence values associated with depth map 602) may be accounted for as weighting operations are performed.

Returning to FIG. 5, along with data obtained as part of object map 800, weighting performed at operation 514 may further take spatial data for each pixel unit into account. For example, it may be determined that a user generally positions a vantage point of an image capture device such that content of interest is near the center of the field of view of each image frame, rather than on the peripheral (e.g., near the edges) of the image frame. Based on this insight, additional weight may be allotted to pixel units that are in certain spatial areas of the image frame (e.g., near the center, near where the user is detected to be focusing attention in real time, etc.) as compared to the weight allotted to pixel units in other spatial areas (e.g., near the periphery, away from where the user is focusing attention, etc.).

To this end, at operation 522, apparatus 100 may generate a spatial status map based on the image frame obtained at operation 502 (e.g., image frame 600) as well as based on other suitable data such as user gaze data indicative of where a user happens to be focusing attention from moment to moment in real time. A spatial status for each pixel unit (represented as part of a spatial status map generated at operation 522) may indicate whether (or the extent to which) the pixel unit is in an area of relatively high importance that is to be allotted more weight (e.g., an area near the center of the image frame or near where the user gaze is focused at the current time) or the pixel unit is in an area of relatively low spatial importance that is to be allotted less weight (e.g., an area near the periphery or away from the user gaze).

To illustrate, FIG. 9 shows two example spatial status maps 900 (e.g., spatial status maps 900-1 and 900-2) that will be understood to correspond to image frame 600 similar to other data maps described above. To reduce clutter, and because spatial status maps may not necessarily depend on depth or other characteristics of content depicted by image frame 600, the grid of boxes making up spatial status maps 900 are not overlaid onto the imagery of image frame 600 in the same way as illustrated above for other data maps. However, it will be understood that these boxes likewise represent the corresponding pixel units represented by other data maps described above.

In the first example, illustrated by spatial status map 900-1, the spatial status assigned to each pixel unit is shown to indicate a centrality of a position of the pixel unit within the image frame. As such, pixel units proximate to a center 802 of image frame 600 are shown to have spatial status values represented as high single-digit values (e.g., '9', '8', '7', etc.), while pixel unit less proximate to center 802 of image frame 600 are shown to have increasingly lower spatial status values (e.g., '3', '2', '1', '0', etc.), Hence, when spatial status map 900-1 is accounted for in the weighting operations, auto-exposure management may not only be influenced by the depth of different types of objects and their likelihood of producing specular pixels, but may further be influenced by the extent to which different pixel units are near the center of the image frame where the user is presumed to be focusing most of his or her attention.

Spatial status map 900-2 brings yet another factor to bear on what may influence the weighting of the pixel units. Specifically, as shown, a gaze area 804 indicative of where a user is focusing attention may be detected (e.g., in real time) based on eye tracking and/or other techniques. Accordingly, in this example, the spatial status assigned to each pixel unit is shown to indicate a proximity of a position of the pixel unit to gaze area 804 (e.g., rather than to center 802) within the image frame. When spatial status map 900-2 is accounted for in the weighting operations, auto-exposure management may be influenced by the extent to which different pixel units are proximate to where the user is determined to actually be focusing attention at any given moment, even if that area is not precisely at the center of the image frame.

Returning to FIG. 5, operation 514 is shown to include an optional operation 524 in which less weight is allotted to one or more pixel units based on the input data being accounted for (e.g., depth map 602, the saturation status map determined based on specular threshold map 700-2, object map 800, either of spatial status maps 900, etc.), as well as an optional operation 526 in which more weight is allotted to one or more pixel units based on this same input data. Operations 524 and 526 may be performed on a pixel-unit-by-pixel-unit basis in connection with any of the weighting considerations that have been described, and may be considered, in certain examples, to be performed as part of the determining of the frame auto-exposure gain explicitly shown to be performed at operation 528. More particularly, after auto-exposure values and auto-exposure targets have been initially determined at operation 512, weighting performed at operation 514 (e.g., by operations 524 and/or 526) may serve to adjust the pixel auto-exposure values and/or targets in accordance with principles described herein so that, at operation 528, apparatus 100 may determine a weighted frame auto-exposure value and a frame auto-exposure target for image frame 600, and may compute a frame auto-exposure gain for image frame 600 based on the weighted frame auto-exposure value and weighted frame auto-exposure target.

The determining of at least one of the frame auto-exposure value or the frame auto-exposure target as part of determining the frame auto-exposure gain at operation 528 may be based on at least one of the depth map, the object map, the saturation status map (which in turn may be based on the specular threshold map and/or the illuminance fall-off map), and/or any other input data as has been described. For example, as has been described, the frame auto-exposure gain may be determined based on the saturation status map by allotting more weight (operation 526) to pixel units that are not saturated and/or designated to be specular pixel units and by allotting less weight (operation 524) to pixel units that are saturated and/or designated to be specular pixel units. Similarly, as another example, the auto-exposure gain may be determined based on the object map by allotting more weight (operation 526) to tissue sample 404 than is allotted to other content at the scene (e.g., instrument 402 and/or background content 406) and/or by allotting less weight (operation 524) to instrument 402 than is allotted to the other content at the scene (e.g., tissue sample 404 and/or background content 406). As yet another example, the auto-exposure gain may be determined based on the spatial status map by allotting more weight (operation 526) to content near center 802 and/or gaze area 804 and/or by allotting less weight (operation 524) to content more remote from center 802 and/or gaze area 804. As has been described, the total auto-exposure gain may be computed as the ratio between the weighted frame auto-exposure target and the weighted frame auto-exposure value and temporal smoothing may be applied in order to suppress unwanted brightness fluctuation.

At operation 530, apparatus 100 may determine one or more settings for one or more auto-exposure parameters based on the frame auto-exposure gain determined at operation 528. For example, each of various auto-exposure parameter settings may be determined that correspond to a different auto-exposure parameter employed by a particular image capture system in a particular implementation. As described above in relation to image capture system 302, these auto-exposure parameters may include an exposure time parameter, an illumination intensity parameter for a visible light source, an illumination intensity parameter for a non-visible light source, various gain parameters (e.g., an analog gain parameter, an RGB gain parameter, a Bayer gain parameter, etc.), and/or any other auto-exposure parameter described herein or as may serve a particular implementation.

Based on the auto-exposure parameter settings determined at operation 530, auto-exposure management targets may be enforced (e.g., approached, achieved, etc.) for subsequent image frames that are captured. To this end, at operation 532, apparatus 100 may update the auto-exposure parameters to the new settings determined at operation 530 such that subsequent image frames will be captured in accordance with the auto-exposure parameters set to the updated settings. At this point, auto-exposure management for the current image frame (e.g., image frame 600) may be considered to be complete and flow may return to operation 502, where a subsequent image frame of the image frame sequence may be obtained to repeat the process.

It will be understood that, in certain examples, every image frame may be analyzed in accordance with flow diagram 500 to keep the auto-exposure data points and parameters as up-to-date as possible. In other examples, only certain image frames (e.g., every other image frame, every third image frame, etc.) may be so analyzed to conserve processing bandwidth in scenarios where more periodic auto-exposure processing still allows design specifications and targets to be achieved. It will also be understood that auto-exposure effects may tend to lag a few frames behind luminance changes at a scene, since auto-exposure parameter adjustments made based on one particular frame do not affect the exposure of that frame, but rather affect subsequent frames. Based on updates to the auto-exposure parameters (and/or based on maintaining the auto-exposure parameters at their current levels when appropriate), apparatus 100 may successfully manage auto-exposure for image frames being captured by the image capture system, and subsequent image frames may be captured with desirable auto-exposure properties so as to have an attractive and beneficial appearance when presented to users.

Figure 10:
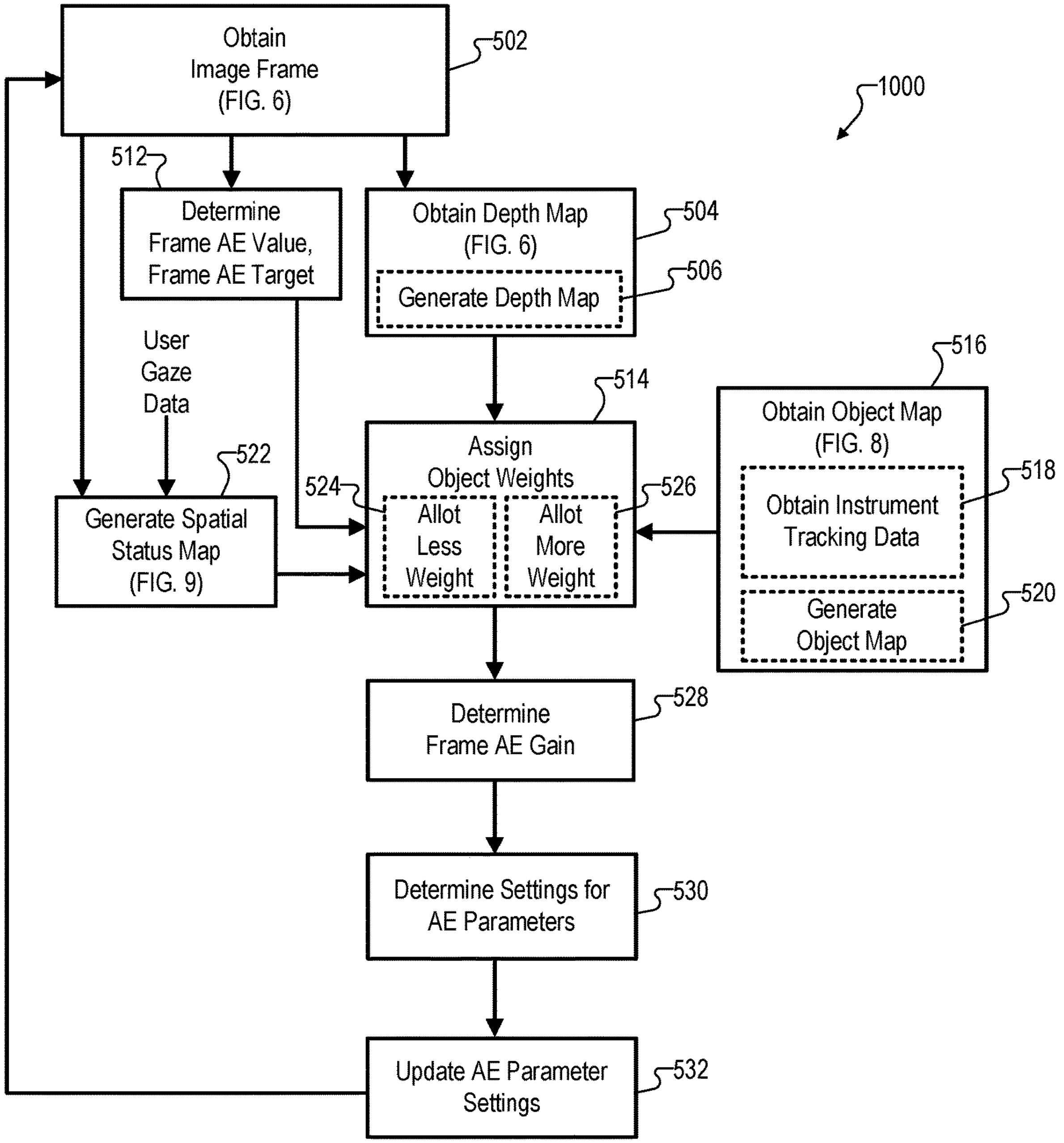
FIGS. 10-11 show other illustrative flow diagrams for depth-based auto-exposure management in accordance with principles described herein.
Figure 11:
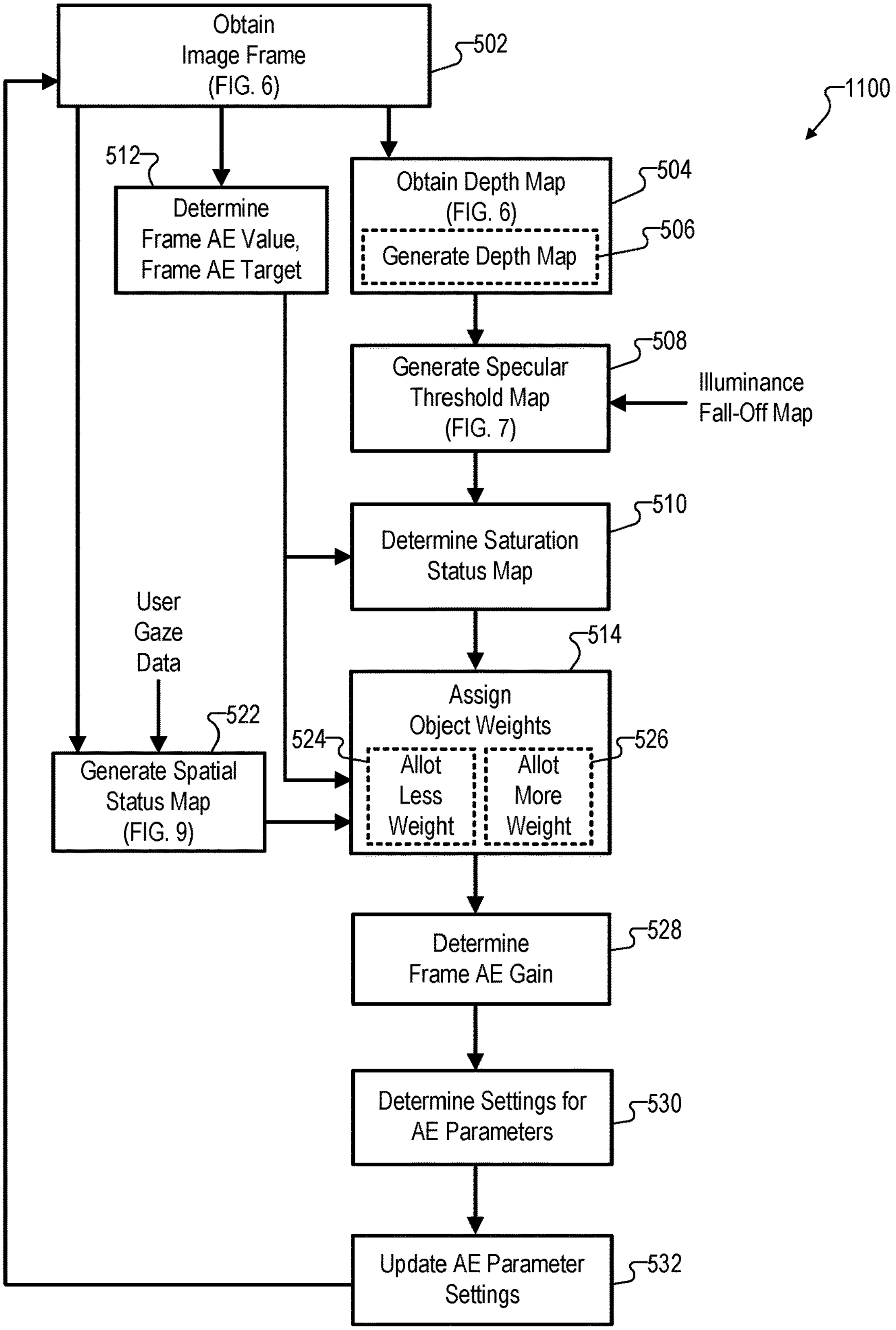

As mentioned above, flow diagram 500 illustrates an implementation in which various types of information including depth information, specular threshold and saturation status information, object correspondence information, spatial status information, and other information may all be accounted for. In other examples, however, it may be possible to achieve desirable outcomes with less complexity and processing than the implementation of flow diagram 500 by incorporating only a subset of this information and not all of it. To illustrate, FIGS. 10 and 11 show illustrative flow diagrams 1000 and 1100, respectively, for depth-based auto-exposure management that operates in accordance with principles described herein but is less complex and/or processing intensive than the implementation of flow diagram 500.

Specifically, as illustrated by flow diagram 1000, one implementation may account directly for depth data obtained within depth map 602 without necessarily incorporating a specular threshold analysis described above. As shown, the implementation illustrated by flow diagram 1000 may also account for object map 800 and one of spatial status maps 900, though it will be understood that, in other examples, one or both of these types of information could also be omitted to further simplify the embodiment if the improvement attained from the depth analysis alone is determined to be adequate for the use case in question.

Similarly, as illustrated by flow diagram 1100, another implementation may use the depth data to perform the specular pixel unit analysis without necessarily incorporating information of an object map such as object map 800 described above. As shown, the implementation illustrated by flow diagram 1100 may also account depth map 602 and one of spatial status maps 900, though it will be understood that, in other examples, one or both of these types of information could also be omitted to further simplify the embodiment if the improvement attained from the specular pixel unit analysis alone are determined to be adequate for the use case in question.

As has been described, apparatus 100, method 200, and/or system 300 may each be associated in certain examples with a computer-assisted medical system used to perform a medical procedure on a body. To illustrate, FIG. 12 shows an illustrative computer-assisted medical system 1200 that may be used to perform various types of medical procedures including surgical and/or non-surgical procedures.

Figure 12:
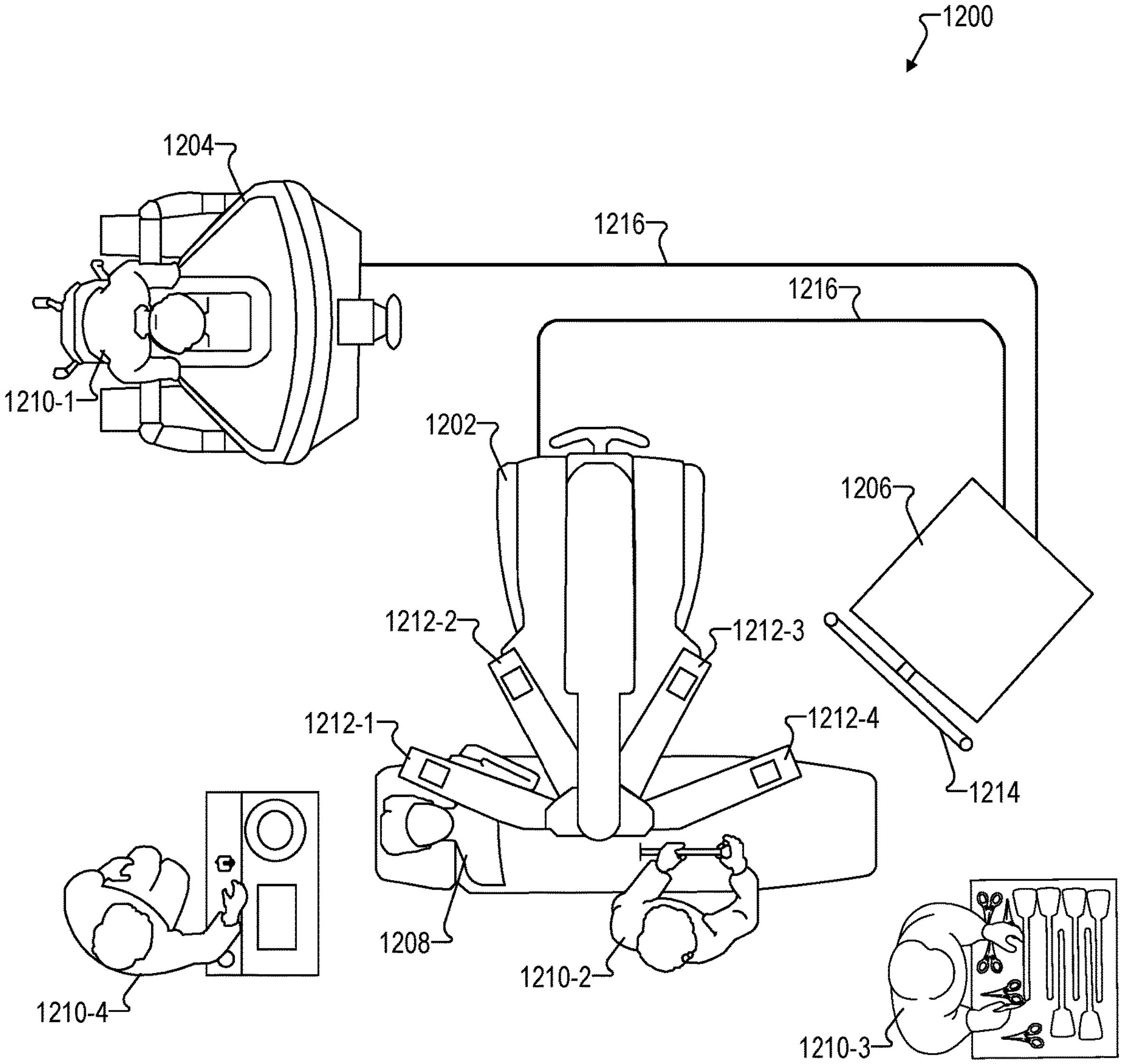
FIG. 12 shows an illustrative computer-assisted medical system according to principles described herein.

As shown, computer-assisted medical system 1200 may include a manipulator assembly 1202 (a manipulator cart is shown in FIG. 12), a user control apparatus 1204, and an auxiliary apparatus 1206, all of which are communicatively coupled to each other. Computer-assisted medical system 1200 may be utilized by a medical team to perform a computer-assisted medical procedure or other similar operation on a body of a patient 1208 or on any other body as may serve a particular implementation. As shown, the medical team may include a first user 1210-1 (such as a surgeon for a surgical procedure), a second user 1210-2 (such as a patient-side assistant), a third user 1210-3 (such as another assistant, a nurse, a trainee, etc.), and a fourth user 1210-4 (such as an anesthesiologist for a surgical procedure), all of whom may be collectively referred to as users 1210, and each of whom may control, interact with, or otherwise be a user of computer-assisted medical system 1200. More, fewer, or alternative users may be present during a medical procedure as may serve a particular implementation. For example, team composition for different medical procedures, or for non-medical procedures, may differ and include users with different roles.

While FIG. 12 illustrates an ongoing minimally invasive medical procedure such as a minimally invasive surgical procedure, it will be understood that computer-assisted medical system 1200 may similarly be used to perform open medical procedures or other types of operations. For example, operations such as exploratory imaging operations, mock medical procedures used for training purposes, and/or other operations may also be performed.

As shown in FIG. 12, manipulator assembly 1202 may include one or more manipulator arms 1212 (e.g., manipulator arms 1212-1 through 1212-4) to which one or more instruments may be coupled. The instruments may be used for a computer-assisted medical procedure on patient 1208 (e.g., in a surgical example, by being at least partially inserted into patient 1208 and manipulated within patient 1208). While manipulator assembly 1202 is depicted and described herein as including four manipulator arms 1212, it will be recognized that manipulator assembly 1202 may include a single manipulator arm 1212 or any other number of manipulator arms as may serve a particular implementation. While the example of FIG. 12 illustrates manipulator arms 1212 as being robotic manipulator arms, it will be understood that, in some examples, one or more instruments may be partially or entirely manually controlled, such as by being handheld and controlled manually by a person. For instance, these partially or entirely manually controlled instruments may be used in conjunction with, or as an alternative to, computer-assisted instrumentation that is coupled to manipulator arms 1212 shown in FIG. 12.

During the medical operation, user control apparatus 1204 may be configured to facilitate teleoperational control by user 1210-1 of manipulator arms 1212 and instruments attached to manipulator arms 1212. To this end, user control apparatus 1204 may provide user 1210-1 with imagery of an operational area associated with patient 1208 as captured by an imaging device. To facilitate control of instruments, user control apparatus 1204 may include a set of master controls. These master controls may be manipulated by user 1210-1 to control movement of the manipulator arms 1212 or any instruments coupled to manipulator arms 1212.

Auxiliary apparatus 1206 may include one or more computing devices configured to perform auxiliary functions in support of the medical procedure, such as providing insufflation, electrocautery energy, illumination or other energy for imaging devices, image processing, or coordinating components of computer-assisted medical system 1200. In some examples, auxiliary apparatus 1206 may be configured with a display monitor 1214 configured to display one or more user interfaces, or graphical or textual information in support of the medical procedure. In some instances, display monitor 1214 may be implemented by a touchscreen display and provide user input functionality. Augmented content provided by a region-based augmentation system may be similar, or differ from, content associated with display monitor 1214 or one or more display devices in the operation area (not shown).

As will be described in more detail below, apparatus 100 may be implemented within or may operate in conjunction with computer-assisted medical system 1200. For instance, in certain implementations, apparatus 100 may be implemented by computing resources included within an instrument (e.g., an endoscopic or other imaging instrument) attached to one of manipulator arms 1212, or by computing resources associated with manipulator assembly 1202, user control apparatus 1204, auxiliary apparatus 1206, or another system component not explicitly shown in FIG. 12.

Manipulator assembly 1202, user control apparatus 1204, and auxiliary apparatus 1206 may be communicatively coupled one to another in any suitable manner. For example, as shown in FIG. 12, manipulator assembly 1202, user control apparatus 1204, and auxiliary apparatus 1206 may be communicatively coupled by way of control lines 1216, which may represent any wired or wireless communication link as may serve a particular implementation. To this end, manipulator assembly 1202, user control apparatus 1204, and auxiliary apparatus 1206 may each include one or more wired or wireless communication interfaces, such as one or more local area network interfaces, Wi-Fi network interfaces, cellular interfaces, and so forth.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory (DRAM), which typically constitutes a main memory. Common forms of computer-readable media include, for example, a disk, hard disk, magnetic tape, any other magnetic medium, a compact disc read-only memory (CD-ROM), a digital video disc (DVD), any other optical medium, random access memory (RAM), programmable read-only memory (PROM), electrically erasable programmable read-only memory (EPROM), FLASH-EEPROM, any other memory chip or cartridge, or any other tangible medium from which a computer can read.

Figure 13:
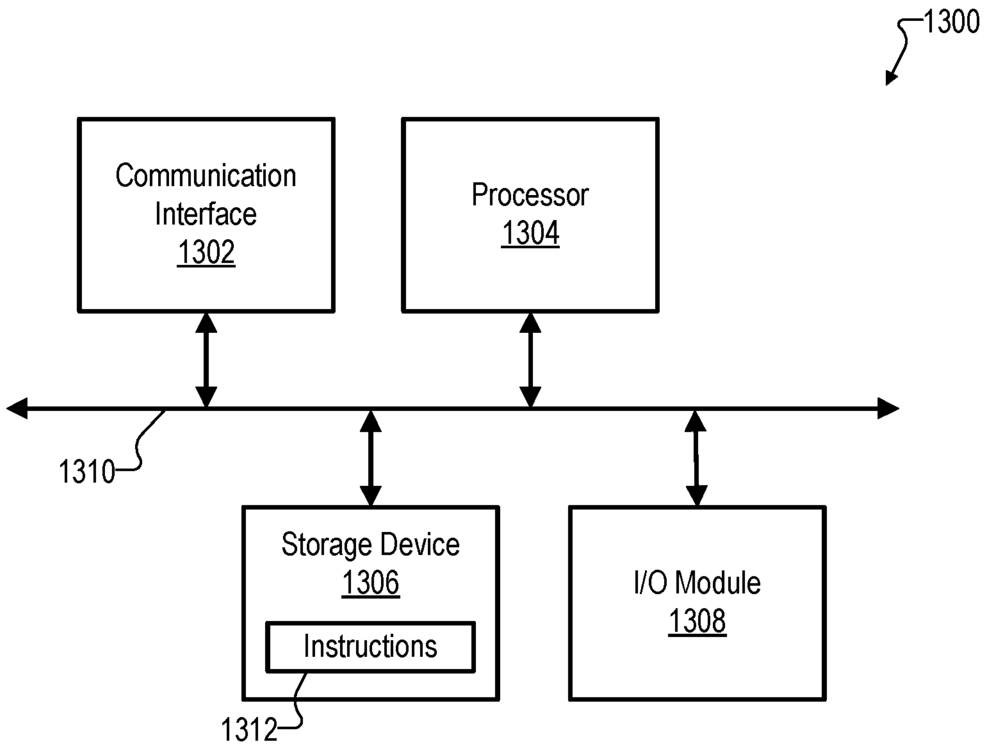
FIG. 13 shows an illustrative computing system according to principles described herein.

FIG. 13 shows an illustrative computing system 1300 that may be specifically configured to perform one or more of the processes described herein. For example, computing system 1300 may include or implement (or partially implement) an auto-exposure management apparatus such as apparatus 100, an auto-exposure management system such as system 300, or any other computing systems or devices described herein.

As shown in FIG. 13, computing system 1300 may include a communication interface 1302, a processor 1304, a storage device 1306, and an input/output (I/O) module 1308 communicatively connected via a communication infrastructure 1310. While an illustrative computing system 1300 is shown in FIG. 13, the components illustrated in FIG. 13 are not intended to be limiting. Additional or alternative components may be used in other embodiments. Components of computing system 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data or interpreting, executing, and/or directing execution of one or more of the instructions, processes, and/or operations described herein. Processor 1304 may direct execution of operations in accordance with one or more applications 1312 or other computer-executable instructions such as may be stored in storage device 1306 or another computer-readable medium.

Storage device 1306 may include one or more data storage media, devices, or configurations and may employ any type, form, and combination of data storage media and/or device. For example, storage device 1306 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1306. For example, data representative of one or more executable applications 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. One or more I/O modules may be used to receive input for a single virtual experience. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing system 1300. For example, one or more applications 1312 residing within storage device 1306 may be configured to direct processor 1304 to perform one or more processes or functions associated with processor 104 of apparatus 100. Likewise, memory 102 of apparatus 100 may be implemented by or within storage device 1306.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:

one or more processors; and memory storing executable instructions that, when executed by the one or more processors, cause the apparatus to:

obtain a depth map corresponding to an image frame captured by an image capture system in accordance with an auto-exposure parameter set to a first setting, the depth map indicating depth values for pixel units of the image frame;

obtain an object map corresponding to the image frame, the object map indicating which of the pixel units depict an object of a predetermined object type;

determine, based on at least one of the depth map or the object map, a frame auto-exposure value and a frame auto-exposure target for the image frame;

compute, based on the frame auto-exposure value and the frame auto-exposure target, an auto-exposure gain associated with the image frame;

determine, based on the auto-exposure gain, a second setting for the auto-exposure parameter; and update the auto-exposure parameter to the second setting such that a subsequent image frame will be captured by the image capture system in accordance with the auto-exposure parameter set to the second setting.

2. The apparatus of claim 1, wherein:

the image capture system comprises a stereoscopic image capture system and the image frame comprises a stereoscopic image frame that includes a left-side version and a right-side version of the image frame; and the obtaining the depth map includes generating the depth map based on differences between corresponding features that are depicted in both the left-side and right-side versions of the image frame.

3. The apparatus of claim 1, wherein:

the depth map includes, for each pixel unit represented in the depth map, a depth value and a confidence value associated with the depth value; and the determining the auto-exposure gain is based on both the depth values and the confidence values included in the depth map.

4. The apparatus of claim 1, wherein:

the image capture system includes an endoscopic image capture device configured to capture internal imagery of a body on which a medical procedure is performed and the image frame depicts a scene internal to the body during the medical procedure;

the predetermined object type comprises tissue of the body and the object comprises a tissue sample from the body that is more proximate to the endoscopic image capture device than is other content at the scene; and the determining the auto-exposure gain includes allotting more weight to the tissue sample than is allotted to the other content at the scene.

5. The apparatus of claim 1, wherein:

the image capture system includes an endoscopic image capture device configured to capture internal imagery of a body on which a medical procedure is performed and the image frame depicts a scene internal to the body during the medical procedure;

the predetermined object type comprises instrumentation for tissue manipulation and the object comprises an instrument at the scene that is more proximate to the endoscopic image capture device than is other content at the scene; and the determining the auto-exposure gain includes allotting less weight to the instrument than is allotted to the other content at the scene.

6. The apparatus of claim 1, wherein:

the image capture system includes an endoscopic image capture device configured to capture internal imagery of a body on which a medical procedure is performed and the image frame depicts a scene internal to the body during the medical procedure;

the predetermined object type comprises instrumentation for tissue manipulation and the object comprises an instrument at the scene; and the obtaining the object map includes obtaining instrument tracking data and generating the object map based on the instrument tracking data.

7. The apparatus of claim 6, wherein the instrument tracking data is based on kinematic parameters used to control the instrument at the scene and is obtained from a computer-assisted medical system controlling the instrument using the kinematic parameters.

8. The apparatus of claim 6, wherein the instrument tracking data is based on computer-vision tracking of the instrument and is obtained from a computer-assisted medical system performing the computer-vision tracking of the instrument.

9. The apparatus of claim 1, wherein:

the instructions further cause the apparatus to generate, based on the depth map, a specular threshold map corresponding to the image frame, the specular threshold map indicating specular thresholds for the pixel units of the image frame; and the determining the auto-exposure gain associated with the image frame is further based on the specular threshold map.

10. The apparatus of claim 1, wherein the determining the auto-exposure gain associated with the image frame includes designating, for each pixel unit of the image frame, a respective weight value determined based on:

a depth of the pixel unit according to the depth map, an object correspondence of the pixel unit according to the object map, and a spatial status of the pixel unit within the image frame.

11. The apparatus of claim 10, wherein the spatial status of the pixel unit indicates a centrality of a position of the pixel unit within the image frame.

12. The apparatus of claim 10, wherein the spatial status of the pixel unit indicates a proximity of a position of the pixel unit to a gaze area within the image frame to which a user is determined to be focusing attention.

13. A method comprising:

obtaining, by a computing device, a depth map corresponding to an image frame captured by an image capture system in accordance with an auto-exposure parameter set to a first setting, the depth map indicating depth values for pixel units of the image frame;

generating, by the computing device and based on the depth map, a specular threshold map corresponding to the image frame, the specular threshold map indicating specular thresholds for the pixel units;

determining, by the computing device and based on the specular threshold map, a frame auto-exposure value and a frame auto-exposure target for the image frame;

computing, by the computing device based on the frame auto-exposure value and the frame auto-exposure target, an auto-exposure gain associated with the image frame;

determining, by the computing device and based on the auto-exposure gain, a second setting for the auto-exposure parameter; and updating, by the computing device, the auto-exposure parameter to the second setting such that a subsequent image frame will be captured by the image capture system in accordance with the auto-exposure parameter set to the second setting.

14. The method of claim 13, wherein:

the image capture system comprises a stereoscopic image capture system and the image frame comprises a stereoscopic image frame that includes a left-side version and a right-side version of the image frame; and the obtaining the depth map includes generating the depth map based on differences between corresponding features that are depicted in both the left-side and right-side versions of the image frame.

15. The method of claim 13, wherein:

the depth map includes, for each pixel unit represented in the depth map, a depth value and a confidence value associated with the depth value; and the determining the auto-exposure gain is based on both the depth values and the confidence values included in the depth map.

16. The method of claim 13, wherein:

the image capture system includes an endoscopic image capture device configured to capture internal imagery of a body on which a medical procedure is performed and the image frame depicts a scene internal to the body during the medical procedure;

the image frame depicts a tissue sample from the body that is more proximate to the endoscopic image capture device than is other content at the scene; and the specular threshold map allots a higher specular threshold to pixel units corresponding to the tissue sample than to pixel units corresponding to the other content at the scene.

17. A system comprising:

an illumination source configured to illuminate tissue within a body during a performance of a medical procedure;

an image capture device configured to capture an image frame in accordance with an auto-exposure parameter set to a first setting, the image frame depicting an internal view of the body that features the tissue illuminated by the illumination source; and one or more processors configured to:

generate, based on a depth map corresponding to the image frame, a specular threshold map corresponding to the image frame, the depth map indicating depth values for pixel units of the image frame and the specular threshold map indicating specular thresholds for the pixel units;

determine, based on the specular threshold map, a frame auto-exposure value and a frame auto-exposure target for the image frame;

compute, based on the frame auto-exposure value and the frame auto-exposure target, an auto-exposure gain associated with the image frame;

determine, based on the auto-exposure gain, a second setting for the auto-exposure parameter; and update the auto-exposure parameter to the second setting such that a subsequent image frame will be captured by the image capture system in accordance with the auto-exposure parameter set to the second setting.

18. The system of claim 17, wherein the generating the specular threshold map is further based on an illuminance fall-off map that indicates how illuminance within the internal view of the body depicted by the image frame decreases as a function of distance from the illumination source.

19. The system of claim 17, wherein:

the one or more processors are further configured to obtain an object map corresponding to the image frame, the object map indicating which of the pixel units depict an object of a predetermined object type; and the determining the auto-exposure gain associated with the image frame is further based on the depth map and the object map.

* * * * *